(12) United States Patent
Ahlmark et al.

(10) Patent No.: US 8,318,785 B2
(45) Date of Patent: Nov. 27, 2012

(54) PHARMACEUTICAL COMPOUNDS

(75) Inventors: Marko Ahlmark, Espoo (FI); Reijo Bäckström, Helsinki (FI); Anne Luiro, Helsinki (FI); Jarmo Pystynen, Espoo (FI); Eija Tiainen, Espoo (FI)

(73) Assignee: Orion Corporation, Espoo (FI)

( * ) Notice: Subject to any disclaimer, the term of this patent is extended or adjusted under 35 U.S.C. 154(b) by 832 days.

(21) Appl. No.: 11/995,878

(22) PCT Filed: Jul. 17, 2006

(86) PCT No.: PCT/FI2006/000257
§ 371 (c)(1),
(2), (4) Date: Nov. 26, 2008

(87) PCT Pub. No.: WO2007/010085
PCT Pub. Date: Jan. 25, 2007

(65) Prior Publication Data
US 2009/0209532 A1 Aug. 20, 2009
US 2011/0086852 A2 Apr. 14, 2011

Related U.S. Application Data

(60) Provisional application No. 60/699,898, filed on Jul. 18, 2005.

(51) Int. Cl.
*A01N 43/80* (2006.01)
*A01N 43/26* (2006.01)
*A01N 43/12* (2006.01)
*A61K 31/425* (2006.01)
*A61K 31/385* (2006.01)
*A61K 31/38* (2006.01)

(52) U.S. Cl. ......... 514/367; 514/373; 514/439; 514/443

(58) Field of Classification Search .................. None
See application file for complete search history.

(56) References Cited

U.S. PATENT DOCUMENTS

| | | | |
|---|---|---|---|
| 3,973,608 A | 8/1976 | Umezawa et al. | |
| 4,198,415 A | 4/1980 | Kornfeld et al. | |
| 4,665,206 A | 5/1987 | Redpath et al. | |
| 5,389,653 A | 2/1995 | Bernauer et al. | |
| 5,426,191 A | 6/1995 | Walker | |
| 5,446,194 A | 8/1995 | Backstrom et al. | |
| 5,446,294 A | 8/1995 | Bayraktaroglu | |
| 5,863,936 A | 1/1999 | Gaeta et al. | |
| 6,150,412 A | 11/2000 | Pystynen et al. | |
| 6,207,706 B1 | 3/2001 | Aperia et al. | |
| 6,512,136 B1 | 1/2003 | Benes et al. | |
| 6,723,754 B2 | 4/2004 | Aho et al. | |
| 2004/0009573 A1 | 1/2004 | Strobel et al. | |

FOREIGN PATENT DOCUMENTS

| | | |
|---|---|---|
| DE | 38 32 846 | 3/1990 |
| DE | 38 32 848 | 3/1990 |
| EP | 0 165 810 | 12/1987 |
| JP | 07-002733 | 1/1995 |
| JP | 2005-145859 | 6/2005 |
| JP | 2005-331913 | 12/2005 |
| WO | WO 96/02537 | 2/1996 |
| WO | WO 96/37456 A1 | 11/1996 |
| WO | WO 97/20837 | 6/1997 |
| WO | WO 98/50382 | 11/1998 |
| WO | WO 00/16777 | 3/2000 |
| WO | WO 00/73269 | 12/2000 |
| WO | WO 01/01984 | 1/2001 |
| WO | WO 01/32762 | 5/2001 |
| WO | WO 01/98250 A1 | 12/2001 |
| WO | WO 01/98251 A1 | 12/2001 |
| WO | WO 02/02548 A1 | 1/2002 |
| WO | WO 02/22551 A1 | 3/2002 |
| WO | WO 03/035621 | 5/2003 |
| WO | WO 03/062392 | 7/2003 |
| WO | WO 03/076420 | 9/2003 |
| WO | WO 2004/041201 | 5/2004 |
| WO | WO 2004/058747 | 7/2004 |
| WO | WO 2004/089897 | 10/2004 |
| WO | WO 2004/108713 | 12/2004 |
| WO | WO 2004/112729 A2 | 12/2004 |
| WO | WO 2005/058228 A2 | 6/2005 |
| WO | WO 2006/051154 A1 | 5/2006 |

OTHER PUBLICATIONS

Bohm et al. "Scaffold hopping", DrugDisc.TodayTech., 2004, vol. 1, issue 3, pp. 217-224.*
Silver "Clinical experience with the novel levodopa formulation entacapone + levodopa + carbidopa (Stalevo®)", Exp.Rev. Neurotherapeut., 2004, vol. 4, issue 4, pp. 589-599.*
Borchardt, R. T. et al. "Catechol O-methyltransferase. 12. Affinity Labeling the Active Site with the Oxidation Products of 5,6-Dihydroxyindole," *Journal of Medicinal Chemistry* (1982) 25(3):263-271.
CAPLUS English Abstract for DE 3832846, Accession No. 1990:437687.
CAPLUS English Abstract for DE 3832848, Accession No. 1990:531990.
CAPLUS English Abstract for JP 07-002733, Accession No. 1995:424937.

(Continued)

*Primary Examiner* — Jeffrey S. Lundgren
*Assistant Examiner* — Stephanie Springer
(74) *Attorney, Agent, or Firm* — Finnegan, Henderson, Farabow, Garrett & Dunner, LLP

(57) ABSTRACT

Compounds of formula (I) exhibit COMT enzyme inhibiting activity and are thus useful as COMT inhibitors.

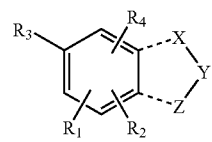

I

28 Claims, No Drawings

OTHER PUBLICATIONS

CAPLUS English Abstract for JP 2005-331913, Accession No. 2005:1261399.
CAPLUS English Abstract for WO 2001/032762, Accession No. 2001:338621.
CAPLUS English Abstract for WO 97/20837, Accession No. 1997:491500.
David, E. et al. "Efficient Access to 2-Aryl-3-Substituted Benzo[b]thiophenes" *J. Org. Chem.* (2005) 70:3569-.
Hemker, H. C. "Inhibition of Adenosine Triphosphatase and Respiration of Rat-Liver Mitochondria by Dinitrophenols" *Biochim. Biophys. Acta* (1964) 81:1.
International Search Report dated Feb. 5, 2007, for International Application No. PCT/FI2006/000257.
Learmonth, D. A. et al. "Synthesis and Biological Evaluation of a Novel Series of "Ortho-Nitrated" Inhibitors of Catechol-*O*-methyltransferase," *Journal of Medicinal Chemistry* (2005) 48(25):8070-8078.
Learmonth, D. A. et al. "Synthesis, Biological Evaluation, and Molecular Modeling Studies of a Novel, Peripherally Selective Inhibitor of Catechol-*O*-methyltransferase." *Journal of Medicinal Chemistry* (2004)47(25):6207-6217.
Lotta, T. et al. "PLS modelling of structure-activity relationships of catechol *O*-methyltransferase inhibitors" *J. Comput-Aided Mol. Design* (1992) 6:253.
Lyubchanskaya, V.M. et al. "2-Benzyl(isobutyl)-5-hydroxybenzofuran derivatives: synthesis and antiviral activity," *Chemical Abstracts Service*, Columbus, Ohio. Database accession No. 1990:35594.
Nissinen, E. et al. "Entacapone, a novel catechol-*O*-methyltransferase inhibitor for Parkinson's disease, does not impair mitochondrial energy production" *Eur. J. Pharmacol.* (1997) 340:287.
Palkowitz, A. D. et al. "Discovery and Synthesis of [6-Hydroxy-3-[4-[2-(1-piperidinyl)ethoxy]phenoxy]-2-(4-hydroxyphenyl)]benzo[b]thiophene: A Novel, Highly Potent, Selective Estrogen Receptor Modulator" *J. Med. Chem.* (1997) 40:1407.
Pouzet, P. et al. "Synthesis of (4-Chlorophenyl)-(1-oxo-1$\lambda^4$benzo[b]thien-2-yl)methanone and study of its reactivity towards sulfur- and oxygen-containing nucleophiles" *Tetrahedron* (1998) 54:14811.
Taskinen, J. et al "QSAR and Binding Model for the Inhibition of Rat Liver Catechol-O-Methyl-Transfersase by 1,5-Substituted-3,4-Dihydroxybenzenes" *Quant. Struct.-Act. Relat.* (1989) 8:210.
Tervo, A. J. et al. "A structure-activity relationship study of catechol-*O*-methyltransferase inhibitors combining molecular docking and 3D QSAR methods" *J. Comput-Aided Mol. Des.* (2003) 17:797.
Borgulya, J. et al. "Catechol-*O*-methyltransferase-Inhibiting Pyrocatechol Derivatives: Synthesis and Structure-Activity Studies," *Helvetica Chimica Acta* 72: 952-968 (1989).
Männisto, P.T. et al. "Properties of Novel Effective and Highly Selective Inhibitors of Catechol-O-Methyltransferase," *Life Sciences* 43(18): 1465-1471 (1988).
Shinagawa, Y. "Molecular Orbital Studies on the Structure-Activity Relationships of Catechol-O-Methyltransferase Inhibitors," *Japan J. Pharmacol.* 58: 95-106 (1992).
CAPLUS Abstract of WO 03/076420, dated Sep. 18, 2003.

\* cited by examiner

PHARMACEUTICAL COMPOUNDS

This application is a national stage filing under 35 U.S.C. §371 of International Application No. PCT/FI2006/000257, filed on Jul. 17, 2006, which claims the benefit of priority of U.S. Application No. 60/699,898 filed on Jul. 18, 2005. The contents of each application are incorporated herein by reference.

FIELD OF THE INVENTION

The present invention relates to pharmacologically active benzofused five-membered heterocycles, or pharmaceutically acceptable salts and esters thereof, as well as to pharmaceutical compositions containing them and to their use as inhibitors of catechol-O-methyltransferase (COMT) enzyme.

BACKGROUND OF THE INVENTION

It is generally known and accepted in the art that COMT inhibitors are useful in the treatment of Parkinson's disease. COMT inhibitors have been shown to be effective in clinical use for the treatment of Parkinson's disease as an adjunct to levodopa therapy. In order to achieve a steady plasma concentration of levodopa, it is desirable that the COMT inhibitor has a good bioavailability and a long duration of action. However, the commercially available COMT inhibitors are associated with a rather short duration of action and their oral bioavailability is limited.

COMT inhibitors have also been indicated to be useful in the treatment of, for example, hypertension, heart failure and depression (cf. e.g. U.S. Pat. No. 5,446,194) as well as inhibitors for the prevention of diabetic vascular dysfunctions (cf. U.S. Pat. No. 6,207,706). COMT inhibitors have also been disclosed as being useful for treating or controlling pain (cf. U.S. Pat. No. 6,723,754) as well as for treating restless legs syndrome (RLS), which is also known as Ekbom's syndrome (cf. WO 2006/051154). RLS is characterized by an irresistible urge to move the legs accompanied by other unpleasant sensations deep within the legs.

Some compounds with COMT inhibiting activity are known in the art. For example, catechol derivatives as COMT inhibitors have been disclosed e.g. in U.S. Pat. No. 5,389,653; U.S. Pat. No. 5,446,194; U.S. Pat. No. 6,150,412; U.S. Pat. No. 6,512,136; WO 01/98250; WO 01/98251; WO 02/02548; U.S. Pat. No. 6,903,114, WO 2004/112729 and WO 2005/058228. Isoflavone derivatives as COMT inhibitors have been disclosed in U.S. Pat. No. 3,973,608.

As to known benzofused five-membered heterocycles, 2-benzyl-7-bromo-6-nitro-benzofuran-4,5-diol has been disclosed in Lyubchanskaya et al. *Khimiko-Farmatsevticheskii Zhurnal*, 23 (1989) 843.

SUMMARY OF THE INVENTION

An object of the present invention is to provide further inhibitors of catechol-O-methyltransferase enzyme that can be used for the treatment of diseases or conditions wherein inhibition of COMT is indicated to be useful. Accordingly, an object of the present invention is to provide further compounds to be used as COMT inhibiting agents in the treatment of mammals, including humans and animals. Furthermore, pharmaceutical compositions containing the present compounds are provided.

Due to slow elimination via glucuronidation, the COMT inhibitors of the present invention have an improved bioavailability and/or a prolonged duration of action. Additionally, the compounds of the present invention possess enhanced primary pharmacological properties, i.e. COMT inhibiting activity. Furthermore, the compounds do not uncouple oxidative phosphorylation and thus possess a desirable safety profile.

DETAILED DESCRIPTION OF THE INVENTION

The present invention relates to novel COMT inhibitors having the general formula I,

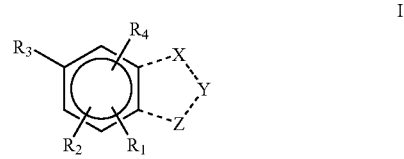

wherein
$R_2$ is in a position ortho to $R_3$ and $R_1$ is in a position ortho to $R_2$ or $R_1$ is in a position ortho to $R_3$ and $R_4$ is in a position ortho to $R_1$;
$R_1$ is cyano or nitro;
$R_2$ is hydroxy;
$R_3$ is hydroxy;
$R_4$ is H, $(C_1-C_6)$alkyl, halo$(C_1-C_6)$alkyl, cyano, formyl, $(C_1-C_6)$alkyl-$(C=O)$—, halogen or nitro;
the dotted line represents a single or a double bond;
two of X, Y or Z are independently $CR_5(R_6)_m$, $N(R_7)_n$, O or S and one of X, Y or Z is $N(R_7)_n$, O or S;
m is, independently at each occurrence, 0 or 1;
n is, independently at each occurrence, 0, 1 or 2;
$R_5$ is, independently at each occurrence, H, $(C_1-C_6)$alkyl, $(C_2-C_6)$alkenyl, halogen, hydroxy, $(C_1-C_6)$alkoxy, halo$(C_1-C_6)$alkyl, hydroxy$(C_1-C_6)$alkyl, $(C_1-C_6)$alkyl-$(C=O)$—, $(C_1-C_8)$alkoxy-$(C=O)$—, cyano, formyl, $(C_1-C_6)$alkyl-$(C=S)$—, $(R_8)_2N$—$(C=S)$—, $R_8$—$(C=NR_8)$—, carboxy, $(C_3-C_7)$cycloalkyl, heterocyclyl, aryl, heteroaryl, heterocyclyl-$(C=O)$—, aryl$(C_1-C_6)$alkyl, $(R_8)_2N$—, $(R_8)_2N$—$(C_1-C_6)$alkyl, $(R_8)_2N$—$(C=O)$—, $(C_1-C_6)$alkyl-S—, $R_9$—$(S=O)$—, $R_9$—$(O=S=O)$—, $(C_1-C_6)$alkoxy$(C_1-C_6)$alkyl, $(C_1-C_6)$alkoxy-$(C=O)$—$(C_1-C_6)$alkyl, $(C_1-C_6)$alkyl-$(C=O)$—O—, $(C_1-C_6)$alkyl-$(C=O)$—O—$(C_1-C_6)$alkyl, hydroxy$(C_1-C_6)$alkoxy$(C_1-C_6)$alkyl, $(C_1-C_6)$alkyl-S—$(C_1-C_6)$alkyl, $(C_1-C_6)$alkyl-S—$(C=O)$—, $(C_3-C_7)$cycloalkyl$(C_1-C_6)$alkyl, aryloxy, aryloxy$(C_1-C_6)$alkyl, aryl$(C_1-C_6)$alkoxy, aryl$(C_1-C_6)$alkoxy$(C_1-C_6)$alkyl or heterocyclyl-$(C=S)$—, wherein said $(C_3-C_7)$cycloalkyl, heterocyclyl, aryl or heteroaryl as such or as part of another group is unsubstituted or substituted with 1, 2 or 3 substituent(s) each independently being $(C_1-C_6)$alkyl, halogen, hydroxy, carboxy, $(C_1-C_6)$alkoxy or $(R_8)_2N$—; $R_6$ is, independently at each occurrence, H, $(C_1-C_6)$alkyl, halogen, hydroxy, hydroxy$(C_1-C_6)$alkyl or $(C_1-C_6)$alkoxy;
or $R_5$ and $R_6$ both attached to the same carbon ring atom form, together with the carbon ring atom to which they are attached, a —$(C=O)$— group; or $R_5$ and $R_6$ both attached to the same carbon ring atom form, together with the carbon ring atom to which they are attached, $C=C(R_8)_2$;
or $R_5$ and $R_6$ both attached to the same carbon ring atom form, together with the carbon ring atom to which they are attached, a 5, 6 or 7 membered saturated or unsaturated carbocyclic ring, wherein said ring is unsubstituted or substituted with 1 or 2 substituent(s) each independently being $(C_1-C_6)$alkyl, halogen, hydroxy, $(C_1-C_6)$alkoxy or carboxy;

$R_7$ is, independently at each occurrence, H, $(C_1-C_6)$alkyl, $(C_3-C_7)$cycloalkyl, $(C_1-C_6)$alkoxy, aryl or O⁻, wherein said $(C_3-C_7)$cycloalkyl or aryl is unsubstituted or substituted with 1, 2 or 3 substituent(s) each independently being $(C_1-C_6)$alkyl, halogen, hydroxy, $(C_1-C_6)$alkoxy or carboxy;

or $R_5$ and $R_5$, $R_5$ and $R_7$, or $R_7$ and $R_7$ attached to adjacent ring atoms form, together with the ring atoms to which they are attached, a condensed 5, 6 or 7 membered saturated or unsaturated carbocyclic ring or a condensed 5, 6 or 7 membered saturated or unsaturated heterocyclic ring containing 1 or 2 heteroatom(s) selected from N, O and S, wherein said carbo- or heterocyclic ring is unsubstituted or substituted with 1 or 2 substituent(s) each independently being $(C_1-C_6)$alkyl, halogen, hydroxy, $(C_1-C_6)$alkoxy, carboxy or oxo;

$R_8$ is, independently at each occurrence, H, $(C_1-C_6)$alkyl, $(C_1-C_6)$alkoxy, aryl or aryl$(C_1-C_6)$alkyl, wherein said aryl as such or as part of another group is unsubstituted or substituted with 1 or 2 substituent(s) each independently being $(C_1-C_6)$alkyl, halogen, hydroxy, carboxy or $(C_1-C_6)$alkoxy;

$R_9$ is, independently at each occurrence, $(C_1-C_6)$alkyl, $(R_8)_2$N—, hydroxy or $(C_1-C_6)$alkoxy; or a pharmaceutically acceptable salt or ester thereof;

with the proviso that the compound is not 2-benzyl-7-bromo-6-nitro-benzofuran-4,5-diol.

In a possible subgroup of the compounds of formula I, $R_2$ is in a position ortho to $R_3$ and R is in a position ortho to $R_2$.

In another possible subgroup of the compounds of formula I, $R_1$ is in a position ortho to $R_3$ and $R_4$ is in a position ortho to $R_1$.

In another possible subgroup of the compounds of formula I, $R_4$ is H, halogen or nitro, for example, H.

In another possible subgroup of the compounds of formula I, $R_1$ is cyano.

In another possible subgroup of the compounds of formula I, $R_1$ is nitro.

In yet another possible subgroup of the compounds of formula I, one of the dotted lines represents a double bond.

In a further possible subgroup of the compounds of formula I, two of X, Y or Z are $CR_5(R_6)_m$ and one of X, Y or Z is N.

In a further possible subgroup of the compounds of formula I, one of X, Y or Z is $CR_5(R_6)_m$, one of X, Y or Z is $N(R_7)_n$, and one of X, Y or Z is S.

In a further possible subgroup of the compounds of formula I, two of X, Y or Z are $CR_5(R_6)_m$ and one of X, Y or Z is O.

In a further possible subgroup of the compounds of formula I, two of X, Y or Z are $CR_5(R_6)_m$ and one of X, Y or Z is S.

In another possible subgroup of the compounds of formula I, $R_7$ is, independently at each occurrence, H, $(C_1-C_6)$alkyl or aryl, wherein said aryl is unsubstituted or substituted with 1, 2 or 3 substituent(s) each independently being halogen.

In yet another possible subgroup of the compounds of formula I, $R_5$ is, independently at each occurrence, H, $(C_1-C_6)$alkyl, halogen, halo$(C_1-C_6)$alkyl, $(C_1-C_9)$alkoxy-(C=O)—, carboxy, aryl, heteroaryl, heterocyclyl-(C=O)— or $(R_8)_2$N—(C=O)—, wherein said heterocyclyl, aryl or heteroaryl as such or as part of another group is unsubstituted or substituted with 1, 2 or 3 substituent(s) each independently being $(C_1-C_6)$alkyl or hydroxy, $R_6$ is, independently at each occurrence, H, or $R_5$ and $R_6$ both attached to the same carbon ring atom form, together with the carbon ring atom to which they are attached, a —(C=O)— group, and $R_8$ is, independently at each occurrence, $(C_1-C_6)$alkyl or aryl, wherein said aryl is unsubstituted or substituted with 1 or 2 substituent(s) each independently being carboxy or $(C_1-C_6)$alkoxy, for example, m is, independently at each occurrence, 0, $R_5$ is, independently at each occurrence, H, halogen, $(C_1-C_8)$alkoxy-(C=O)—, carboxy, heterocyclyl-(C=O)— or $(R_8)_2$N—(C=O)—, wherein said heterocyclyl as part of another group is unsubstituted or substituted with 1, 2 or 3 substituent(s) each independently being $(C_1-C_6)$alkyl or hydroxy, and $R_8$ is, independently at each occurrence, $(C_1-C_6)$alkyl or aryl, wherein said aryl is unsubstituted or substituted with 1 substituent being carboxy or $(C_1-C_6)$alkoxy.

In a further possible subgroup of the compounds of formula I, the compound is 2-(4-chloro-phenyl)-5,6-dihydroxy-4-nitro-2,3-dihydro-isoindol-1-one, 5,6-dihydroxy-7-nitro-3H-isobenzofuran-1-one, 7-nitro-2-pyridin-4-yl-benzothiazole-5,6-diol, methane sulfonate, 3-chloro-5,6-dihydroxy-7-nitro-benzo[b]thiophene-2-carboxylic acid, 3-chloro-5,6-dihydroxy-7-nitro-benzo[b]thiophene-2-carboxylic acid ethyl ester, 3-chloro-5,6-dihydroxy-4-nitro-benzo[b]thiophene-2-carboxylic acid, 3-chloro-5,6-dihydroxy-7-nitro-benzo[b]thiophene, (3-chloro-5,6-dihydroxy-7-nitro-benzo[b]thiophen-2-yl)-morpholin-4-yl-methanone, 3-chloro-5,6-dihydroxy-7-nitro-benzo[b]thiophene-2-carboxylic acid diethylamide, (3-chloro-5,6-dihydroxy-7-nitro-benzo[b]thiophen-2-yl)-piperidin-1-yl-methanone, 3-chloro-5,6-dihydroxy-7-nitro-benzo[b]thiophene-2-carboxylic acid phenylamide, 3-[(3-chloro-5,6-dihydroxy-7-nitro-benzo[b]thiophene-2-carbonyl)-amino]-benzoic acid, 4-[(3-chloro-5,6-dihydroxy-7-nitro-benzo[b]thiophene-2-carbonyl)-amino]-benzoic acid, 3-chloro-5,6-dihydroxy-7-nitro-benzo[b]thiophene-2-carboxylic acid (4-methoxy-phenyl)amide, 2-methyl-7-nitro-benzothiazole-5,6-diol, (5,6-dihydroxy-7-nitro-benzo[b]thiophen-2-yl)-morpholin-4-yl-methanone, 5,6-dihydroxy-7-nitro-benzo[b]thiophene-2-carboxylic acid, 5,6-dihydroxy-7-nitro-benzofuran-2-carboxylic acid, 5,6-dihydroxy-2-methyl-7-nitro-benzo[d]isothiazol-3-one, (5,6-dihydroxy-3-methyl-7-nitro-benzo[b]thiophen-2-yl)morpholin-4-yl-methanone, 5,6-dihydroxy-7-nitro-benzo[b]thiophene-2-carboxylic acid ethyl ester, 5,6-dihydroxy-4-nitro-isobenzofuran-1,3-dione, 5,6-dihydroxy-4-nitro-3H-isobenzofuran-1-one, 5,6-dihydroxy-4,7-dinitro-3H-isobenzofuran-1-one, 7-nitro-2-phenyl-benzothiazole-5,6-diol, 6,7-dihydroxy-5-nitro-benzo[b]thiophene-2-carboxylic acid methyl ester, 1-(5,6-dimethoxy-7-nitro-benzo[b]thiophen-2-yl)-nonan-1-one, (3-chloro-5,6-dihydroxy-4,7-dinitro-benzo[b]thiophen-2-yl)-morpholin-4-yl-methanone, (3,4-chloro-5,6-dihydroxy-7-dinitro-benzo[b]thiophen-2-yl)-morpholin-4-yl-methanone, (3-chloro-5,6-dihydroxy-4-nitro-benzo[b]thiophen-2-yl)-morpholin-4-yl-methanone, (3-chloro-5,6-dihydroxy-7-nitro-benzo[b]thiophen-2-yl)-(2,6-dimethyl-morpholin-4-yl)-methanone, (3-chloro-5,6-dihydroxy-7-nitro-benzo[b]thiophen-2-yl)-(4-hydroxy-piperidin-1-yl)-methanone, (3-bromomethyl-5,6-dihydroxy-7-nitro-benzo[b]thiophen-2-yl)-morpholin-4-yl-methanone, 5,6-dihydroxy-3-methyl-2-(morpholine-4-carbonyl)-benzo[b]thiophene-4-carbonitrile or (3-chloro-5,6-dihydroxy-7-cyano-benzo[b]thiophen-2-yl)-morpholin-4-yl-methanone.

It is evident to a person skilled in the art that, in the compounds of formula I, at least one of two bonds represented by a dotted line and having a common atom represented by X, Y or Z is a single bond and that the aromatic character of the six-membered ring is retained.

Likewise, it is evident to a person skilled in the art that, in the compounds of formula I, when the substituent $R_7$ is O⁻, the nitrogen atom, to which said substituent is attached, is a positively charged quaternary nitrogen atom.

The terms employed herein have the following meanings:

The term "cyano", as employed herein, refers to a —CN group.

The term "nitro", as employed herein, refers to a —NO$_2$ group.

The term "($C_1$-$C_6$)alkyl", as employed herein as such or as part of another group, refers to a straight or branched chain saturated hydrocarbon group having 1, 2, 3, 4, 5 or 6 carbon atom(s). Representative examples of ($C_1$-$C_6$)alkyl include, but are not limited to, methyl, ethyl, n-propyl, iso-propyl, n-butyl, iso-butyl, sec-butyl, tert-butyl, n-pentyl, iso-pentyl, and n-hexyl.

The term "halo" or "halogen", as employed herein as such or as part of another group, refers to fluorine, chlorine, bromine or iodine.

The term "halo($C_1$-$C_6$)alkyl", as employed herein, refers to at least one halogen, as defined herein, appended to the parent molecular moiety through an ($C_1$-$C_6$)alkyl group, as defined herein. Representative examples of halo($C_1$-$C_6$)alkyl include, but are not limited to, fluoromethyl, chloromethyl, difluoromethyl, trifluoromethyl, 2-chloroethyl, 3-bromopropyl, and 2-chloropropyl.

The term "formyl", as employed herein, refers to a —CHO group.

The term "hydroxy", as employed herein as such or as part of another group, refers to a —OH group.

The term "($C_1$-$C_6$)alkoxy", as employed herein as such or as part of another group, refers to an ($C_1$-$C_6$)alkyl group, as defined herein, appended to the parent molecular moiety through an oxygen atom. Representative examples of ($C_1$-$C_6$) alkoxy include, but are not limited to methoxy, ethoxy, n-propoxy, n-butoxy, iso-butoxy, sec-butoxy, and tert-butoxy.

The term "($C_1$-$C_8$)alkoxy", as employed herein as part of another group, refers to a straight or branched chain saturated hydrocarbon group having 1, 2, 3, 4, 5, 6, 7 or 8 carbon atom(s) appended to the parent molecular moiety through an oxygen atom. Representative examples of ($C_1$-$C_8$)alkoxy include, but are not limited to methoxy, ethoxy, n-propoxy, n-butoxy, iso-butoxy, sec-butoxy, tert-butoxy, and n-octoxy.

The term "hydroxy($C_1$-$C_6$)alkoxy", as employed herein as part of another group, refers to at least one hydroxy group, as defined herein, appended to the parent molecular moiety through an ($C_1$-$C_6$)alkoxy group, as defined herein. Representative examples of hydroxy($C_1$-$C_6$)alkoxy include, but are not limited to, hydroxymethoxy, dihydroxymethoxy, 2-hydroxyethoxy, 2-hydroxypropoxy, and 2-hydroxy-1-methylethoxy.

The term "($C_3$-$C_7$)cycloalkyl", as employed herein as such or as part of another group, refers to a saturated cyclic hydrocarbon group containing 3, 4, 5, 6 or 7 carbon atoms. Representative examples of ($C_3$-$C_7$)cycloalkyl include, but are not limited to, cyclopropyl, cyclopentyl, and cyclohexyl.

The term "($C_2$-$C_6$)alkenyl", as employed herein, refers to a straight or branched chain hydrocarbon group having 2, 3, 4, 5 or 6 carbon atoms and containing at least one carbon-carbon double bond. Representative examples of ($C_2$-$C_6$)alkenyl include, but are not limited to, ethenyl and 2-propenyl.

The term "aryl", as employed herein as such or as part of another group, refers to a mono- or bicyclic aromatic carbocyclic group containing 6 or 10 carbon atoms.

The term "aryl($C_1$-$C_6$)alkyl", as employed herein, refers to an aryl group, as defined herein, appended to the parent molecular moiety through an ($C_1$-$C_6$)alkyl group, as defined herein. Representative examples of aryl($C_1$-$C_6$)alkyl include, but are not limited to, phenylmethyl and naphth-1-ylmethyl.

The term "hydroxy($C_1$-$C_6$)alkyl", as employed herein, refers to at least one hydroxy group, as defined herein, appended to the parent molecular moiety through an ($C_1$-$C_6$) alkyl group, as defined herein. Representative examples of hydroxy($C_1$-$C_6$)alkyl include, but are not limited to, hydroxymethyl, 1-hydroxyethyl, 2,2-dihydroxyethyl, 1-hydroxypropyl, 3-hydroxypropyl, 1-hydroxy-1-methylethyl, and 1-hydroxy-1-methylpropyl.

The term "heterocyclyl", as employed herein as such or as part of another group, refers to a 5, 6 or 7 membered saturated cyclic group containing 1 or 2 heteroatom(s) each independently selected from N, O, and S. Representative examples of heterocyclyl include, but are not limited to, pyrrolidinyl, piperidinyl, piperazinyl, morpholinyl, and azepanyl.

The term "carboxy", as employed herein, refers to a —COOH group.

The term "heteroaryl", as employed herein, refers to a 5, 6 or 7 membered aromatic group containing 1, 2, 3 or 4 heteroatom(s) each independently selected from N, O, and S. Representative examples of heteroaryl include, but are not limited to, pyrrolyl, furanyl, thiophenyl, imidazolyl, oxazolyl, thiazolyl, triazolyl, tetrazolyl, pyrazolyl, pyridinyl, pyrimidinyl, pyrazinyl, pyridazinyl, pyranyl, and azepinyl.

The term "($C_1$-$C_6$)alkoxy($C_1$-$C_6$)alkyl", as employed herein as such or as part of another group, refers to at least one ($C_1$-$C_6$)alkoxy group, as defined herein, appended to the parent molecular moiety through an ($C_1$-$C_6$)alkyl group, as defined herein. Representative examples of ($C_1$-$C_6$)alkoxy ($C_1$-$C_6$)alkyl include, but are not limited to, methoxymethyl, propoxymethyl, 2-ethoxyethyl, 2,2-dimethoxyethyl, 1-methyl-2-propoxyethyl and 4-methoxybutyl.

The term "aryl($C_1$-$C_6$)alkoxy", as employed herein as such or as part of another group, refers to an aryl group, as defined herein, appended to the parent molecular moiety through an ($C_1$-$C_6$)alkoxy group, as defined herein. Representative examples of aryl($C_1$-$C_6$)alkoxy include, but are not limited to, phenylmethoxy, 2-phenylethoxy, and 2-naphth-2-ylethoxy.

The term "oxo", as employed herein, refers to a =O group.

Pharmaceutically acceptable salts, e.g. metal salts and acid addition salts, with both organic and inorganic acids, are well known in the field of pharmaceuticals. Representative examples of pharmaceutically acceptable metal salts include, but are not limited to, lithium, sodium, potassium, calcium, magnesium, aluminum and zinc salts. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, and ascorbates.

Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, n-propyl, iso-propyl, n-butyl, iso-butyl, sec-butyl, and tert-butyl esters.

The invention includes within its scope all the possible geometric isomers, e.g. Z and E isomers (cis and trans isomers), of the compounds as well as all the possible optical isomers, e.g. diastereomers and enantiomers, of the compounds. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof conventional resolution methods, e.g. fractional crystallization, may be used.

The compounds of formula I can be prepared by a variety of synthetic routes analogously to or according to methods known in the literature using suitable starting materials.

Benzofuran derivatives can be prepared, for example, according to reaction scheme 1:

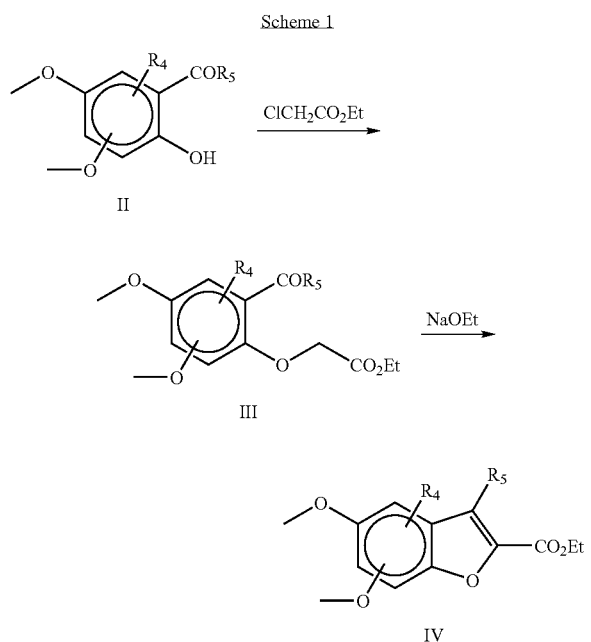

In scheme 1 the methoxy substituents are in a position ortho to each other, $R_4$ is as defined above and in a position ortho to either the acyl substituent or the hydroxy substituent in formula II, and $R_5$ is as defined above. An acylphenol compound is alkylated with a functionalized haloderivative at room temperature in the presence of a suitable base in a suitable solvent, e.g. potassium carbonate in N,N-dimethylformamide or sodium hydride in tetrahydrofuran. The activated methylene group is condensed with the carbonyl by using a suitable base, e.g. sodium ethanolate. In addition to the carbethoxy group, the methylene group can be activated with any methylene activating group like nitro, cyano, acyl, aryl, aryloxy, alkylthio, or arylthio. The carbethoxy group can then be converted to other functional groups, if desired.

The preparation of benzofuran derivatives is further exemplified in Example 18.

2,3-Dihydro-isoindol-1-one derivatives can be prepared, for example, according to reaction scheme 2:

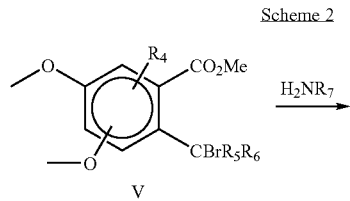

-continued

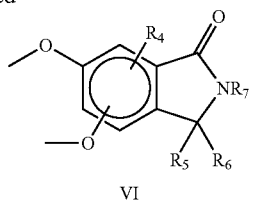

In scheme 2 the methoxy substituents are in a position ortho to each other, $R_4$ is as defined above and in a position ortho to either the methoxycarbonyl substituent or the $CBrR_5R_6$-substituent in formula V, and $R_5$, $R_6$, and $R_7$ are as defined above. The ring is formed by refluxing a compound of formula V with an amine in a suitable solvent, e.g. toluene.

The preparation of 2,3-dihydro-isoindol-1-one derivatives is further exemplified in Example 1.

Benzothiazole derivatives can be prepared, for example, according to scheme 3:

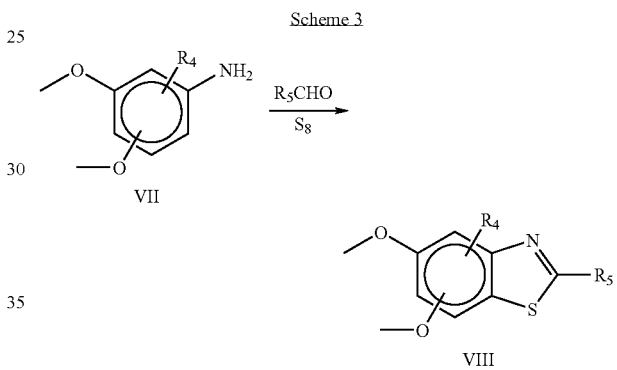

In scheme 3 the methoxy substituents are in a position ortho to each other, $R_4$ is as defined above and in a 4- or 7-position in formula VIII, and $R_5$ is, for example, aryl or heteroaryl. The ring is formed by refluxing an aniline with an aldehyde and elementary sulfur in a suitable solvent, e.g. dimethyl acetamide.

The preparation of benzothiazole derivatives is further exemplified in Examples 3, 15 and 25.

Benzo[b]thiophene derivatives can be prepared, for example, according to reaction scheme 4:

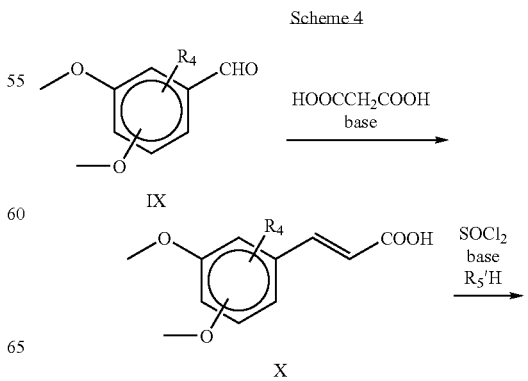

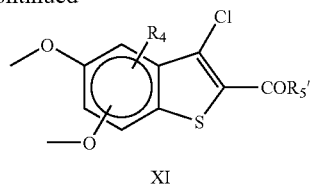

XI

In scheme 4 the methoxy substituents are in a position ortho to each other, $R_4$ is as defined above and in a 4- or 7-position in formula XI, and $R_5'$ is, for example, ($C_1$-$C_8$) alkoxy, N-containing heterocyclyl or $(R_8)_2N$—, wherein $R_8$ is as defined above. A benzaldehyde is condensed with malonic acid in a suitable solvent, e.g. pyridine, resulting in an acrylic acid derivative. The ring is formed by reacting the acid with thionyl chloride in a suitable solvent, e.g. chlorobenzene or toluene.

Another route for preparing benzo[b]thiophene derivatives is illustrated in scheme 5:

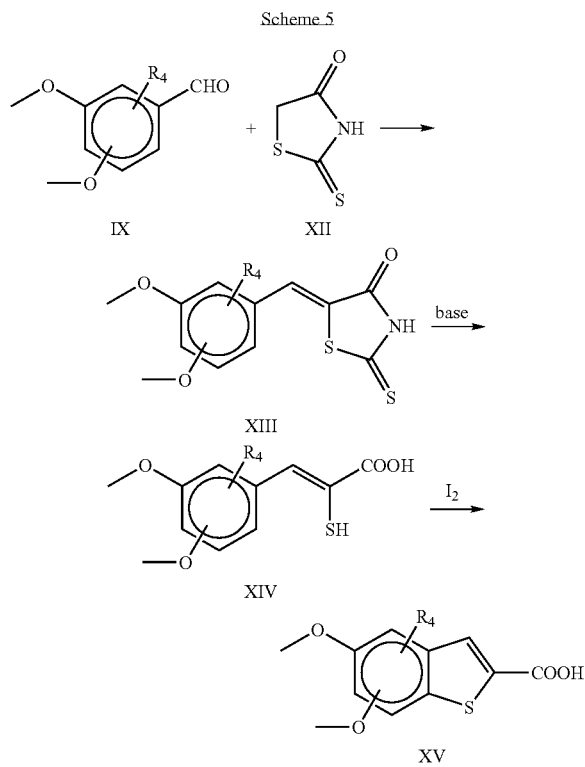

In scheme 5 the methoxy substituents are in a position ortho to each other. A benzaldehyde is condensed with rhodanine XII in a suitable solvent, e.g. a carboxylic acid such as acetic acid, resulting in intermediate XIII. With the aid of a suitable base, e.g. sodium hydroxide, the intermediate is converted into a 2-mercapto-acrylic acid derivative. The ring is formed by treating the mercapto compound with, for example, iodine in a suitable solvent, e.g. tetrahydrofuran. The carboxy group can then be converted to other functional groups, if desired.

The preparation of benzo[b]thiophene derivatives is further exemplified in Examples 4-14, 16-17, 20-21, and 26-35.

The dealkylation of the resulting dialkoxy intermediates as well as the insertion of the substituent $R_1$ being cyano or nitro is described in the specific compound examples.

It is obvious for a person skilled in the art that any starting material or intermediate in the reactions described above can be protected, if necessary, in a manner well known in the chemical field. Any protected functionality can subsequently be deprotected in a manner known in the art.

The synthetic routes described above are meant to illustrate the preparation of the compounds of formula I and the preparation is by no means limited thereto, i.e. there are also other possible synthetic methods which are within the general knowledge of a person skilled in the art.

The compounds of formula I may be converted, if desired, into their pharmaceutically acceptable salt or ester form using methods well known in the art.

The present invention will be explained in more detail by the following examples. The examples are meant for illustrating purposes only and do not limit the scope of the invention defined in the claims.

Example 1

2-(4-Chloro-phenyl)-5,6-dihydroxy-4-nitro-2,3-dihydro-isoindol-1-one 2-(4-Chloro-phenyl)-5,6-dimethoxy-2,3-dihydro-isoindol-1-one A solution of 2-bromomethyl-4,5-dimethoxy-benzoic acid methyl ester (2.9 g), 4-chloroaniline (1.28 g) and triethylamine (1.4 ml) was refluxed in toluene for six hours. The reaction mixture was stirred in an ice bath, filtered and washed with 1 M hydrochloric acid and water.
Yield: 0.74 g
$^1$H NMR (DMSO-$d_6$): δ=3.85 (s, 3H, $CH_3O$), 3.88 (s, 3H, $CH_3O$), 4.89 (s, 2H, $CH_2$), 7.23 (s, 1H, ArH), 7.24 (s, 1H, ArH), 7.48 (d, 2H, J=8.9 Hz), 7.91 (d, 2H, J=8.9 Hz).

2-(4-Chloro-phenyl)-5,6-dihydroxy-2,3-dihydro-isoindol-1-one 2-(4-Chloro-phenyl)-5,6-dimethoxy-2,3-dihydro-isoindol-1-one (0.74 g) was demethylated with 4 eq of boron tribromide as described in Example 8.
Yield: 0.79 g (raw material used as such in the next step)
$^1$H NMR (DMSO-$d_6$): δ=4.80 (s, 2H, $CH_2$), 6.77 (s, 1H, ArH), 6.82 (s, 1H, ArH), 7.48 (d, 2H, J=9.1 Hz), 7.91 (d, 2H, J=9.1 Hz).

Acetic acid 6-acetoxy-2-(4-chloro-phenyl)-3-oxo-2,3-dihydro-1H-isoindol-5-yl ester 2-(4-Chloro-phenyl)-5,6-dihydroxy-2,3-dihydro-isoindol-1-one (0.79 g of raw material) and acetic anhydride (10 ml) was stirred in 80° C. with one drop of sulfuric acid as a catalyst for one hour. The mixture was poured into ice water, filtered and recrystallized from acetic acid.
Yield: 0.5 g
$^1$H NMR (DMSO-$d_6$): δ=2.29 (s, 3H, $CH_3COO$), 2.34 (s, 3H, $CH_3COO$), 5.04 (s, 2H, $CH_2$), 7.51 (d, 2H, J=8.8 Hz), 7.62 (s, 1H, ArH), 7.70 (s, 1H, ArH), 7.92 (d, 2H, J=8.8 Hz).

Acetic acid 2-(4-chloro-phenyl)-6-hydroxy-3-oxo-2,3-dihydro-1H-isoindol-5-yl ester A solution of acetic acid 6-acetoxy-2-(4-chloro-phenyl)-3-oxo-2,3-dihydro-1H-isoindol-5-yl ester (0.5 g) in dry N,N-dimethylformamide (15 ml) was treated with morpholine (0.13 ml) at 0-5° C. and stirred then for an hour at room temperature. The reaction was poured into ice water and filtered.

Yield: 0.34 g $^1$H NMR (DMSO-d$_6$): δ=2.29 (s, 3H, CH$_3$COO), 4.92 (s, 2H, CH$_2$), 7.14 (s, 1H, ArH), 7.43 (s, 1H, ArH), 7.48 (d, 2H, J=8.9 Hz), 7.90 (d, 2H, J=8.9 Hz).

Acetic acid 2-(4-chloro-phenyl)-6-hydroxy-7-nitro-3-oxo-2,3-dihydro-1-isoindol-5-yl ester A suspension of acetic acid 2-(4-chloro-phenyl)-6-hydroxy-3-oxo-2,3-dihydro-1H-isoindol-5-yl ester (0.34 g) in acetic acid (7 ml) was treated with 2 M nitric acid in dichloromethane (0.6 ml). After an hour the reaction mixture was filtered.

Yield: 0.24 g (raw material used as such in the next step)

$^1$H NMR (DMSO-d$_6$): δ=2.35 (s, 3H, CH$_3$COO), 5.25 (s, 2H, CH$_2$), 7.50 (d, 2H, J=8.8 Hz), 7.89 (s, 1H, ArH), 7.93 (d, 2H, J=8.8 Hz).

2-(4-Chloro-phenyl)-5,6-dihydroxy-4-nitro-2,3-dihydro-isoindol-1-one

Acetic acid 2-(4-chloro-phenyl)-6-hydroxy-7-nitro-3-oxo-2,3-dihydro-1H-isoindol-5-yl ester (0.24 g raw material) was refluxed in methanol (15 ml) with three drops of concentrated hydrochloric acid for six hours. The reaction mixture was cooled and filtered.

Yield: 80 mg $^1$H NMR (DMSO-d$_6$): δ=5.13 (s, 2H, CH$_2$), 7.34 (s, 1H, ArH), 7.48 (d, 2H, J=8.7 Hz), 7.91 (d, 2H, J=8.7 Hz), 10.4-11.5 (b, 2H, OH).

Example 2

5,6-Dihydroxy-7-nitro-3H-isobenzofuran-1-one 5,6-Dihydroxy-7-nitro-3H-isobenzofuran-1-one To a solution of 5,6-dihydroxy-3H-isobenzofuran-1-one (0.4 g) in sulfuric acid at −30° C. was added 5 M nitric acid in sulfuric acid (0.55 ml). The reaction mixture was let to warm up to room temperature and then poured into ice water. The product was filtered and recrystallized from acetic acid.

Yield: 0.2 g $^1$H NMR (DMSO-d$_6$): δ=5.26 (s, 2H, CH2), 7.14 (s, 1H, ArH), 10.6 (b, 1H, OH), 11.75 (b, 1H, OH).

Example 3

7-Nitro-2-pyridin-4-yl-benzothiazole-5,6-diol, methane sulfonate 5,6-Dimethoxy-2-pyridin-4-yl-benzothiazole A solution of 3,4-dimethoxyaniline (6 g) and sulfur (5 g) were refluxed in 4-picolin (15 ml) for five hours. The cool reaction mixture was poured into methanol, kept over ice bath for 30 minutes and filtered. The product was washed with methanol and carbon disulfide.

Yield: 6.14 g $^1$H NMR (DMSO-d$_6$): δ=3.88 (s, 3H, CH$_3$O), 3.89 (s, 3H, CH$_3$O), 7.67 (s, 1H, ArH), 7.76 (s, 1H, ArH), 7.94 (d, 2H, J=6.4 Hz), 8.75 (d, 2H, J=6.4 Hz).

5,6-Dimethoxy-4-nitro-2-pyridin-4-yl-benzothiazole

To a solution of 5,6-dimethoxy-2-pyridin-4-yl-benzothiazole (1.1 g) in sulfuric acid (10 ml) was added potassium nitrate (0.5 g). After 60 minutes in room temperature the mixture was poured into ice water and filtered. Recrystallization from acetone yielded the pure product.

Yield: 0.8 g $^1$H NMR (DMSO-d$_6$): δ=4.05 (s, 3H, CH$_3$O), 4.07 (s, 3H, CH$_3$O), 8.07 (d, 2H, J=6 Hz), 8.25 (s, 1H, ArH), 8.81 (d, 2H, J=6 Hz).

7-Nitro-2-pyridin-4-yl-benzothiazole-5,6-diol, methane sulfonate

A solution of 5,6-dimethoxy-4-nitro-2-pyridin-4-yl-benzothiazole (0.4 g) was refluxed in 48% HBr (14.5 ml) for two hours. The crystals were filtered, taken in methanesulfonic acid (2 ml) by warming and diluted with methanol. After stirring in ice bath the salt was filtered.

Yield: 0.44 g

Melting point: >350° C.

$^1$H NMR (DMSO-d$_6$): δ=2.37 (s, 3H, CH$_3$SO$_3$—), 7.83 (s, 1H, ArH), 8.42 (d, 2H, J=6.3 Hz), 8.94 (d, 2H, J=6.3 Hz).

Example 4

3-Chloro-5,6-dihydroxy-7-nitro-benzo[b]thiophene-2-carboxylic acid 3-(3,4-Dimethoxy-phenyl)acrylic acid 3,4-Dimethoxybenzaldehyde (5 g), malonic acid (4.7 g), piperidine (0.5 ml) and pyridine (15 ml) were refluxed for six hours. The reaction mixture was poured into ice-cold water and acidified with 6M hydrochloric acid. The resultant solid was filtered, washed with water and dried under vacuum.

$^1$H NMR (DMSO-d$_6$): δ=3.80 (d, 6H), 6.44 (d, 1H), 7.20 (q, 1H), 7.31 (d, 1H), 7.4 (d, 1H), 12 (br, 1H).

3-Chloro-5,6-dimethoxy-benzo[b]thiophene-2-carboxylic acid methyl ester 3-(3,4-Dimethoxy-phenyl)acrylic acid (1.0 g) was slurried in chlorobenzene (25 ml) and then thionyl chloride (1.5 ml) was added. The suspension was stirred at room temperature and after 30 min pyridine (0.1 ml) was added. The reaction mixture was refluxed for 24 hours. The resultant solid was filtered and dissolved in chlorobenzene (20 ml) and methanol (20 ml). The reaction mixture was refluxed for one hour and then cooled. The solid was filtered, washed with methanol and dried under vacuum.

$^1$H NMR (DMSO-d$_6$): δ=3.88 (s, 3H), 3.89 (s, 3H), 3.90 (s, 3H), 7.29 (s, 1H), 7.29 (s, 1H), 7.68 (s, 1H).

3-Chloro-5,6-dihydroxy-benzo[b]thiophene-2-carboxylic acid

3-Chloro-5,6-dimethoxy-benzo[b]thiophene-2-carboxylic acid methyl ester (0.2 g) was suspended in dichloromethane (10 ml) under nitrogen, cooled to −20° C. and boron tribromide (0.4 ml) was added. The resultant mixture was stirred at −20° C. for 30 min and then in cool overnight. The mixture was poured into ice-cold water, extracted into ethyl acetate and evaporated to dryness. The product was used for the next step without any purification.

3-Chloro-5,6-dihydroxy-7-nitro-benzo[b]thiophene-2-carboxylic acid

3-Chloro-5,6-dihydroxy-benzo[b]thiophene-2-carboxylic acid was dissolved in ethyl acetate and a solution of nitric acid in dichloromethane (2M, 0.38 ml) was gradually added at 20° C. The solution was stirred 10 min at room temperature and then it was poured into ice-cold water and extracted with ethyl acetate. The organic extracts were combined, dried and evaporated to dryness. The residue was recrystallized from acetic acid.

Yield: 94 mg
Melting point: 298-300° C.
$^1$H NMR (DMSO-d$_6$): δ=7.49 (s, 1H), 13-14 (br, 1H).

Example 5

3-Chloro-5,6-dihydroxy-7-nitro-benzo[b]thiophene-2-carboxylic acid ethyl ester

3-Chloro-5,6-dihydroxy-7-nitro-benzo[b]thiophene-2-carboxylic acid ethyl ester

3-Chloro-5,6-dihydroxy-7-nitro-benzo[b]thiophene-2-carboxylic acid (70 mg) from Example 4, ethanol (2 ml) and thionyl chloride (0.16 ml) were refluxed for 4 hours. Ethanol was evaporated. The residue was heated with absolute ethanol and the hot mixture was filtered. The product was dried under vacuum.

Yield: 34 mg
Melting point: 215° C.
$^1$H NMR (DMSO-d$_6$): δ=1.36 (t, 3H), 4.36 (q, 2H) 7.50 (s, 1H).

Example 6

3-Chloro-5,6-dihydroxy-4-nitro-benzo[b]thiophene-2-carboxylic acid

3-Chloro-5-benzyloxy-6-methoxy-benzo[b]thiophene-2-carboxylic acid methyl ester 3-(3-Benzyloxy-4-methoxy-phenyl)acrylic acid was converted to 3-chloro-5-benzyloxy-6-methoxy-benzo[b]thiophene-2-carboxylic acid methyl ester by repeating the method of Example 4, except that 3-(3-benzyloxy-4-methoxy-phenyl)acrylic acid was used instead of 3-(3,4-dimethoxy-phenyl)acrylic acid. The product was a mixture of two compounds and it was used for the next step without any purification.

3-Chloro-5-hydroxy-6-methoxy-benzo[b]thiophene-2-carboxylic acid methyl ester

3-Chloro-5-benzyloxy-6-methoxy-benzo[b]thiophene-2-carboxylic acid methyl ester (0.7 g), acetic acid (17.5 ml) and concentrated hydrochloride acid (2.1 ml) was refluxed for six hours. The mixture was cooled and evaporated to dryness. The resultant mixture was extracted first into diethyl ether and then into a solution of 1M sodium hydroxide. The water phase was acidified with 6M hydrochloric acid. The solution was stirred in cool for two hours and filtered. The solid was washed with water and dried under vacuum. The product was a mixture of two compounds and it was used for the next step without any purification.

3-Chloro-5-hydroxy-6-methoxy-benzo[b]thiophene-2-carboxylic acid

3-Chloro-5-hydroxy-6-methoxy-benzo[b]thiophene-2-carboxylic acid methyl ester (0.5 g) was dissolved in methanol (10 ml) and 5M sodium hydroxide (10 ml) added to. The solution refluxed for two hours. Methanol was evaporated and the resultant solution was acidified with 2M hydrochloric acid. The resultant solid was dried under vacuum. The product was used for the next step without any purification.

3-Chloro-5-hydroxy-6-methoxy-4-nitro-benzo[b]thiophene-2-carboxylic acid

3-Chloro-5-hydroxy-6-methoxy-benzo[b]thiophene-2-carboxylic acid (0.28 g) was dissolved in ethyl acetate and a solution of nitric acid in dichloromethane (2M, 0.75 ml) was gradually added at 20° C. into. The solution was stirred at room temperature for 10 min and then it was poured into ice-cold water and extracted with ethyl acetate and evaporated to dryness.

$^1$H NMR (DMSO-d$_6$): δ=3.98 (s, 3H), 7.90 (s, 1H) 10.9 (br, 1H), 13.4-14.4 (br, 1H).

3-Chloro-5,6-dihydroxy-4-nitro-benzo[b]thiophene-2-carboxylic acid

To the solution of 3-chloro-5-hydroxy-6-methoxy-4-nitro-benzo[b]thiophene-2-carboxylic acid (0.2 g), pyridine (6.3 ml) in ethyl acetate (5 ml) was gradually added aluminum trichloride (0.32 g). The reaction mixture was refluxed at 90° C. for two hours. To the warm reaction (60° C.) solution was added the mixture of concentrated hydrochloric acid and ice (1:1). The product was extracted into ethyl acetate, dried and evaporated. The residue was treated with diethyl ether and the resultant solid was filtered.

Yield: 32 mg
Melting point: 215-219° C.
$^1$H NMR (DMSO-d$_6$): δ=7.54 (s, 1H), 10-12 (br, 2H), 13.5-14 (br, 1H)

Example 7

3-Chloro-5,6-dihydroxy-7-nitro-benzo[b]thiophene

3-Chloro-6-benzyloxy-5-methoxy-benzo[b]thiophene-2-carboxylic acid methyl ester 3-(4-Benzyloxy-3-methoxy-phenyl)acrylic acid was converted to 3-chloro-6-benzyloxy-5-methoxy-benzo[b]thiophene-2-carboxylic acid methyl ester by repeating the method of Example 4, except that 3-(4-benzyloxy-3-methoxy-phenyl)acrylic acid was used instead of 3-(3,4-dimethoxy-phenyl)acrylic acid.

$^1$H NMR (DMSO-d$_6$): δ=3.88 (s, 3H), 3.90 (s, 3H), 5.20 (s, 2H) 7.32-7.50 (m, 5H), 7.81 (s, 1H).

3-Chloro-6-hydroxy-5-methoxy-benzo[b]thiophene

3-Chloro-6-benzyloxy-5-methoxy-benzo[b]thiophene-2-carboxylic acid methyl ester (1.33 g), methanol (27 ml) and 5M sodium hydroxide (27 ml) were refluxed for 2.5 hours. Methanol was evaporated and the resultant solid was filtered. The solid was dissolved in water and acidified with concentrated hydrochloric acid. The mixture was stirred in an ice-water bath, filtered and dried in vacuum. The resultant solid, copper (0.17 g) and quinoline (10.6 ml) were heated at 21° C. for one hour. To the cooled mixture was added 10% hydrochloric acid (26 ml) and dissolved in ethyl acetate. The solution was washed with 10% sodium carbonate and 1M hydrochloric acid and then it was evaporated to dryness. The residue, acetic acid (24 ml) and concentrate hydrochloric acid (3.2 ml) were refluxed 5 hours. The solution was evaporated to dryness. The residue was dissolved in diethyl ether and then extracted with 1M sodium hydroxide. The water phase was acidified with 6M hydrochloric acid and extracted into ethyl acetate. The solution was dried, evaporated to dryness and then triturated with diethyl ether and filtered.

$^1$H NMR (DMSO-$d_6$): δ=3.89 (s, 3H), 7.17 (s, 1H), 7.35 (s, 1H) 7.56 (s, 1H), 9.52 (s, 1H).

3-Chloro-6-hydroxy-5-methoxy-7-nitro-benzo[b] thiophene

3-Chloro-6-hydroxy-5-methoxy-benzo[b]thiophene (0.39 g) was dissolved in ethyl acetate (26 ml). To the solution was gradually added a solution of nitric acid in dichloromethane (2M, 0.9 ml) at room temperature. The solution was stirred at room temperature for 10 min and then it was poured into ice-cold water and extracted with ethyl acetate and evaporated to dryness. The product was purified by column chromatography using toluene-ethyl acetate-acetic acid 8:1:1 as the eluent.

$^1$H NM (DMSO-$d_6$): δ=4.02 (s, 3H), 7.58 (s, 1H), 7.87 (s, 1H).

3-Chloro-5,6-dihydroxy-7-nitro-benzo[b]thiophene

To the solution of 3-chloro-6-hydroxy-5-methoxy-7-nitro-benzo[b]thiophene (0.13 g) and pyridine (3.3 ml) was gradually added aluminum trichloride (0.09 g). The reaction mixture was heated at 90° C. for 2 hours. To the warm reaction (60° C.) mixture was added the mixture of ice and concentrated hydrochloric acid (1:1). The product was filtered, washed with 1M hydrochloric acid and water and dried under vacuum.

Yield: 110 mg
Melting point: 182-184° C.
$^1$H NMR (DMSO-$d_6$): δ=7.49 (s, 1H), 7.83 (s, 1H) 10-12 (br, 2H).

Example 8

(3-Chloro-5,6-dihydroxy-7-nitro-benzo[b]thiophen-2-yl)-morpholin-4-yl-methanone (3-Chloro-5,6-dimethoxy-benzo[b]thiophen-2-yl)-morpholin-4-yl-methanone 3-(3,4-Dimethoxy-phenyl)acrylic acid was converted to (3-chloro-5,6-dimethoxy-benzo[b]thiophen-2-yl)-morpholin-4-yl-methanone by repeating the method of Example 4, except that morpholine was used instead of methanol.

$^1$H NMR (DMSO-$d_6$): δ=3.53 (m, 4H), 3.64 (m, 4H), 3.85 (s, 3H), 3.88 (s, 3H), 7.21 (s, 1H), 7.67 (s, 1H).

(3-Chloro-5,6-dihydroxy-benzo[b]thiophen-2-yl)-morpholin-4-yl-methanone (3-Chloro-5,6-dimethoxy-benzo[b]thiophen-2-yl)-morpholin-4-yl-methanone (8.6 g) was suspended in dichloromethane (50 ml) under nitrogen, cooled to −20° C. and treated dropwise with 1M boron tribromide (100 ml) in dichloromethane. The resultant suspension was stirred at −20° C. for 30 min and then in cool overnight. The mixture was poured into ice-cold water and stirred for 30 min at room temperature. The product was filtered and washed with water.

$^1$H NMR (DMSO-$d_6$): δ=3.40 (br, 4H), 3.62 (br, 4H), 7.11 (s, 1H), 7.32 (s, 1H), 9.5-10.0 (br, 2H).

(3-Chloro-5,6-dihydroxy-7-nitro-benzo[b]thiophen-2-yl)-morpholin-4-yl-methanone (3-Chloro-5,6-dihydroxy-benzo[b]thiophen-2-yl)-morpholin-4-yl-methanone (7.7 g) was dissolved in ethyl acetate (500 ml) and a solution of nitric acid in dichloromethane (2M, 13.6 ml) was gradually added at 20° C. into. The solution was stirred 30 min at room temperature and then it was poured into ice-cold water and the resultant solid was filtered and dried in vacuum. The product was recrystallized from acetic acid.

Yield: 4.8 g
Melting point: 259° C.
$^1$H NMR (DMSO-$d_6$): δ=3.53 (br, 4H), 3.62 (br, 4H), 7.51 (s, 1H), 10-11 (br, 2H).

Example 9

3-Chloro-5,6-dihydroxy-7-nitro-benzo[b]thiophene-2-carboxylic acid diethylamide 5,6-Diacetoxy-3-chloro-7-nitro-benzo[b]thiophene-2-carboxylic acid 3-Chloro-5,6-dihydroxy-7-nitro-benzo[b]thiophene-2-carboxylic acid (0.32 g) from Example 4, acetanhydride (1.6 ml) and concentrated sulphuric acid (2 drops) were warmed at 50-60° C. for one hour. The reaction mixture was poured into ice-cold water and stirred in cold. The product was filtered, washed with cold water and dried in vacuum.

$^1$H NMR (DMSO-$d_6$): δ=2.41 (s, 3H), 2.48 (s, 3H), 13.5-14.5 (br, 1H)

5,6-Diacetoxy-3-chloro-7-nitro-benzo[b]thiophene-2-carboxylic acid diethylamide

To the solution of 5,6-diacetoxy-3-chloro-7-nitro-benzo[b]thiophene-2-carboxylic acid (0.39 g) in toluene (3.9 ml) was added thionyl chloride (0.11 ml) and N,N-dimethylformamide (one drop). The solution was warmed at 80° C. for one hour and then it was evaporated to dryness and dried under vacuum. The residue was dissolved in dichloromethane (3.9 ml) and the solution of diethylamine (0.12 ml) and N,N-diisopropylamine (0.5 ml) in dichloromethane (3.9 ml) was added. The reaction solution was stirred at room temperature for three hours. It was evaporated to dryness and methanol (5 ml) and concentrated hydrochloric acid (1 ml) were added into the residue. The product was extracted with dichloromethane and after that it was washed with water and the solution of sodium bicarbonate. The solution was dried and evaporated. The product was used for the next step without any purification.

3-Chloro-5,6-dihydroxy-7-nitro-benzo[b]thiophene-2-carboxylic acid diethylamide 5,6-Diacetoxy-3-chloro-7-nitro-benzo[b]thiophene-2-carboxylic acid diethylamide (0.32 g) was dissolved in methanol (16 ml) and a solution of potassium carbonate (0.61 g) in water (3 ml) was added to the reaction solution. It was stirred at room temperature for one hour. Methanol was evaporated and the residue was kept in cool and filtered. The solid was washed with water and recrystallized from methanol.

Yield: 138 mg
Melting point: 202-205° C.
$^1$H NMR (DMSO-$d_6$): δ=1.14 (b, 6H), 3.41 (b, 4H), 7.49 (s, 1H), 10-12 (br, 2H).

Example 10

(3-Chloro-5,6-dihydroxy-7-nitro-benzo[b]thiophen-2-yl)-piperidin-1-yl-methanone

(3-Chloro-5,6-dihydroxy-7-nitro-benzo[b]thiophen-2-yl)-piperidin-1-yl-methanone The title compound was prepared from the product of Example 4 by repeating the method of Example 9, except that piperidine was used instead of diethylamine.

Yield: 192 mg
Melting point: 254-256° C.
$^1$H NMR (DMSO-d$_6$): δ=1.55-1.62 (m, 10H), 7.48 (s, 1H), 10-11 (br, 2H).

Example 11

3-Chloro-5,6-dihydroxy-7-nitro-benzo[b]thiophene-2-carboxylic acid phenylamide

3-Chloro-5,6-dihydroxy-7-nitro-benzo[b]thiophene-2-carboxylic acid phenylamide The title compound was prepared from the product of Example 4 by repeating the method of Example 9, except that aniline was used instead of diethylamine.

Yield: 100 mg
Melting point: 288° C.
$^1$H NMR (DMSO-d$_6$): δ=7.15 (t, 1H), 7.38 (t, 2H), 7.52 (s, 1H), 7.70 (d, 1H), 10.37 (s, 1H).

Example 12

3-[(3-Chloro-5,6-dihydroxy-7-nitro-benzo[b]thiophene-2-carbonyl)-amino]-benzoic acid

3-[(3-Chloro-5,6-dihydroxy-7-nitro-benzo[b]thiophene-2-carbonyl)-amino]-benzoic acid The title compound was prepared from the product of Example 4 by repeating the method of Example 9, except that 3-amino-benzoic acid was used instead of diethylamine.

Yield: 53 mg
Melting point: 293-294° C.
$^1$H NMR (DMSO-d$_6$): δ=7.50 (d, 1H), 7.53 (d, 1H), 7.72 (d, 1H), 7.95 (d, 1H), 8.36 (s, 1H), 10.58 (s, 1H).

Example 13

4-[(3-Chloro-5,6-dihydroxy-7-nitro-benzo[b]thiophene-2-carbonyl)-amino]-benzoic acid

4-[(3-Chloro-5,6-dihydroxy-7-nitro-benzo[b]thiophene-2-carbonyl)-amino]-benzoic acid The title compound was prepared from the product of Example 4 by repeating the method of Example 9, except that 4-amino-benzoic acid was used instead of diethylamine.

Yield: 110 mg
Melting point: 298-300° C.
$^1$H NMR (DMSO-d$_6$): δ=7.55 (s, 1H), 7.84 (d, 2H), 7.96 (d, 2H), 10.70 (s, 1H).

Example 14

3-Chloro-5,6-dihydroxy-7-nitro-benzo[b]thiophene-2-carboxylic acid (4-methoxy-phenyl)amide

3-Chloro-5,6-dihydroxy-7-nitro-benzo[b]thiophene-2-carboxylic acid (4-methoxy-phenyl)amide The title compound was prepared from the product of Example 4 by repeating the method of Example 9, except that 4-methoxy-aniline was used instead of diethylamine.

Yield: 94 mg
Melting point: >350° C.
$^1$H NMR (DMSO-d$_6$): δ=3.74 (s, 3H), 6.88 (s, 1H), 6.92 (d, 2H), 7.62 (d, 2H), 8.46 (br, 2H), 9.82 (br, 1H).

Example 15

2-Methyl-7-nitro-benzothiazole-5,6-diol

1-Bromo-4,5-dimethoxy-2-nitro-benzene

To the solution of 4-bromoveratrole (20 g) in acetic acid (50 ml) was added 2M nitric acid (48 ml). It was stirred at room temperature for 30 min and then the reaction solution was poured into water. The resultant solid was filtered, washed with water and dried in vacuum.

$^1$H NMR (DMSO-d$_6$): δ=3.85 (s, 3H), 3.90 (s, 3H), 7.38 (s, 1H), 7.67 (s, 1H).

5,6-Dimethoxy-2-methyl-benzothiazole

1-Bromo-4,5-dimethoxy-2-nitro-benzene (10 g) was suspended into ethanol (50 ml). To the reaction mixture was added the suspension of sodium sulfide (5 g) and sulfur (0.65 g) in ethanol (12 ml). The reaction mixture was refluxed 1.5 hour and then the resultant solid was filtered and washed with hot water and ethanol. The dry solid was slurried with acetic acid (60 ml) and acetanhydridi (35 ml). To the suspension was gradually added zinc (16.6 g) and the suspension was stirred at room temperature for 15 min before filtering off. The residue was evaporated to dryness. The product was purified by column chromatography using toluene-ethyl acetate-acetic acid 8:1:1 as the eluent.

$^1$H NMR (DMSO-d$_6$): δ=2.72 (s, 3H), 3.81 (s, 3H), 3.82 (s, 3H), 7.44 (s, 1H), 7.56 (s, 1H).

2-Methyl-benzothiazole-5,6-diol 5,6-Dimethoxy-2-methyl-benzothiazole (3.9 g) was refluxed with 47% hydrobromic acid (40 ml) for four hours. The solid was filtered and dried under vacuum.

$^1$H NMR (DMSO-d$_6$): δ=2.66 (s, 3H), 7.21 (s, 1H), 7.33 (s, 1H), 9.23 (s, 2H)

2-Methyl-7-nitro-benzothiazole-5,6-diol

2-Methyl-benzothiazole-5,6-diol was dissolved in ethyl acetate and a solution of nitric acid in dichloromethane (2M, 0.38 ml) was gradually added at 20° C. into. The solution was stirred 10 min at room temperature and then it was poured into ice water and extracted into ethyl acetate and evaporated. The product was purified by column chromatography using toluene-ethyl acetate-acetic acid 8:1:1 as the eluent.

Yield: 75 mg
Melting point: 219° C.
$^1$H NMR (DMSO-d$_6$): δ=2.73 (s, 3H), 7.63 (s, 1H), 10.1-10.9 (br, 2H).

Example 16

(5,6-Dihydroxy-7-nitro-benzo[b]thiophen-2-yl)-morpholin-4-yl-methanone

5-[1-(4-Benzyloxy-3-methoxy-phenyl)-meth-(Z)-ylidene]-2-thioxo thiazolidin-4-one 4-Benzyloxy-3-methoxy-benzaldehyde (29 g) was dissolved in acetic acid (16 g) and then rhodanine (16 g) and sodium acetate (36 g) added into. The solution was refluxed for one hour. The reaction solution was poured into water. The solid was filtered, washed with water and dried under vacuum.

$^1$H NMR (DMSO-d$_6$): δ=3.83 (s, 3H), 5.17 (s, 2H), 7.15-7.22 (q, 3H), 7.33-7.46 (m, 5H), 7.60 (s, 1H), 13.0-14.0 (br, 1H).

(Z)-3-(4-Benzyloxy-3-methoxy-phenyl)-2-mercapto-acrylic acid

5-[1-(4-Benzyloxy-3-methoxy-phenyl)-meth-(Z)-ylidene]-2-thioxo thiazolidin-4-one (38 g) and 2.5M NaOH were warmed at 80° C. for one hour. Next the solution was cooled to 10° C. and poured slowly into 6M HCl-solution (200 ml). The reaction mixture was stirred at room temperature for one hour. The solid was filtered, washed with water and dried under vacuum.

$^1$H NMR (DMSO-d$_6$): δ=3.80 (s, 3H), 5.14 (s, 2H), 7.14-7.16 (d, 1H), 7.26-7.46 (m, 6H), 7.70 (s, 1H).

6-Hydroxy-5-methoxy-benzo[b]thiophene-2-carboxylic acid (Z)-3-(4-Benzyloxy-3-methoxy-phenyl)-2-mercapto-acrylic acid (21 g) and iodine (21 g) in tetrahydrofuran (300 ml) was stirred in 60° C. for 15 hours. Then it was poured into water (1 l) and 120 g sodium bisulfite was added. The product was extracted into ethylacetate and then it extracted into sodium bicarbonate. The water phase was acified by concentrated hydrochloric acid and stirred in room temperature for one hour. The solid was filtered, washed with water and dried under vacuum.

$^1$H NMR (DMSO-d$_6$): δ=3.83 (s, 3H), 7.29 (s, 1H), 7.45 (s, 1H), 7.89 (s, 1H), 9.70 (br, 1H), 12.8-13.3 (br, 1H).

6-Hydroxy-5-methoxy-7-nitro-benzo[b]thiophene-2-carboxylic acid

6-Hydroxy-5-methoxy-benzo[b]thiophene-2-carboxylic acid (3.2 g) was dissolved in ethyl acetate (200 ml) and a solution of nitric acid in dichloromethane (2M, 7.7 ml) was gradually added at 0° C. into. The solution was stirred 30 min at room temperature and then it was poured into ice-cold water and filtered. The solid was washed with ethyl acetate and dried under vacuum.

$^1$H NMR (DMSO-d$_6$): δ=3.96 (s, 3H), 7.95 (s, 1H), 8.05 (s, 1H), 11.5-12.0 (br, 1H), 12.8-13.6 (br, 1H).

(6-Hydroxy-5-methoxy-7-nitro-benzo[b]thiophen-2-yl)-morpholin-4-yl-methanone

6-Hydroxy-5-methoxy-7-nitro-benzo[b]thiophene-2-carboxylic acid (2.7 g) was dissolved in toluene (45 ml). Thionyl chloride (1.2 ml) and N,N-dimethylformamide (4 drops) were added. The solution was stirred at 80° C. for two hours and after that it was evaporated. The residue was dissolved into dichloromethane (45 ml) and morpholine (1.4 ml) and triethylamine (1.2 ml) added. The reaction solution was stirred at room temperature overnight. The solution of water and 2M HCl was added to the solution. The solid was washed with water and dried under vacuum.

$^1$H NMR (DMSO-d$_6$): δ=3.67 (b, 4H), 3.69 (b, 4H), 3.95 (s, 3H), 7.73 (s, 1H), 7.87 (s, 1H), 11.0-11.8 (br, 1H).

(5,6-Dihydroxy-7-nitro-benzo[b]thiophen-2-yl)-morpholin-4-yl-methanone (6-Hydroxy-5-methoxy-7-nitro-benzo[b]thiophen-2-yl)-morpholin-4-yl-methanone (1.0 g) was dissolved in ethyl acetate (11 ml) and pyridine (14 ml) added into. Next aluminum trichloride (0.47 g) was gradually added into the solution. The reaction mixture was refluxed for 2 hours at 110° C. To the warm reaction (60° C.) solution was added the mixture of ice and concentrated hydrochloric acid (1:1) and then it was stirred at room temperature for one hour. The solid was filtered, washed with water and treated with diethyl ether.

Yield: 114 mg

Melting point: 266° C.

$^1$H NMR (DMSO-d$_6$): δ=3.65 (b, 4H), 3.68 (b, 4H), 7.64 (s, 1H), 7.72 (s, 1H), 10-11 (br, 2H).

Example 17

5,6-Dihydroxy-7-nitro-benzo[b]thiophene-2-carboxylic acid

4-Benzyloxy-3-ethoxy-benzaldehyde

To the solution of 3-ethoxy-4-hydroxy-benzaldehyde (83 g) in N,N-dimethylformamide (400 ml) was gradually added 10 M sodium hydroxide (55 ml) and then benzyl chloride (60 ml) was added at a temperature under 40° C. The mixture was stirred at room temperature for a half an hour and for 2 hours at 60° C. The solution was poured into ice-cold water (2 l) and extracted with diethyl ether. The organic phase was washed with water and 5M sodium hydroxide and then it was dried and evaporated. The product was recrystallized from toluene-heptane.

$^1$H NMR (DMSO-d$_6$): δ=1.34 (t, 3H), 4.12 (q, 2H), 5.24 (s, 2H), 7.26 (d, 1H), 7.34-7.53 (m, 7H), 9.83 (s, 1H).

4-Benzyloxy-5-ethoxy-2-nitro-benzaldehyde

4-Benzyloxy-3-ethoxy-benzaldehyde (20 g) was dissolved in dichloromethane (100 ml) and a solution of nitric acid in dichloromethane (2M, 200 ml) was gradually added at a temperature under 30° C. The solution was stirred at room temperature for 10 min and then it was poured into ice-cold water. The organic phase was washed with 1M sodium hydroxide and water and then it was dried and evaporated.

$^1$H NMR (DMSO-d$_6$): δ=1.37 (t, 3H), 4.25 (q, 2H), 5.34 (s, 2H), 7.36-7.49 (m, 5H), 7.82 (s, 1H), 10.19 (s, 1H)

5-Ethoxy-4-hydroxy-2-nitro-benzaldehyde

4-Benzyloxy-5-ethoxy-2-nitro-benzaldehyde (23 g) was dissolved in acetic acid (93 ml) and concentrated hydrochloric acid (10 ml). The reaction solution was refluxed for 24 hours. Then the solution was evaporated to dryness and the residue was dissolved in diethyl ether. The product was extracted into 1M sodium hydroxide and acidified with 6M hydrochloric acid. The resultant solid was filtered and dried under vacuum.

¹H NMR (DMSO-d₆): δ=1.37 (t, 3H), 4.20 (q, 2H), 7.33 (s, 1H), 7.57 (s, 1H), 10.15 (s, 1H), 10.6-11.2 (br, 1H).

5-Ethoxy-4-hydroxy-2,3-dinitro-benzaldehyde

5-Ethoxy-4-hydroxy-2-nitro-benzaldehyde (1.6 g) was dissolved in dichloromethane (30 ml) and a solution of nitric acid in dichloromethane (2M, 13 ml) was gradually added at a temperature under 30° C. The solution was stirred at room temperature for 10 min and then it was poured into ice-cold water. The organic phase was washed with water and then it was dried and evaporated.
¹H NMR (DMSO-d₆): δ=1.41 (t, 3H), 4.32 (q, 2H), 7.56 (s, 1H), 9.93 (s, 1H).

4,5-Diethoxy-2,3-dinitro-benzaldehyde

5-Ethoxy-4-hydroxy-2,3-dinitro-benzaldehyde (3.77 g), N,N-dimethylformamide (35 ml), $K_2CO_3$ (3.877 g) and ethyl bromide (50 ml) were refluxed 24 hours. To the reaction solution was added diethyl ether (100 ml) and then it was washed with water and 1M sodium hydroxide. The solution was dried and evaporated.
¹H NMR (DMSO-d₆): δ=1.26 (t, 3H), 1.43 (t, 3H), 4.36 (m, 6H), 7.70 (s, 1H), 10.05 (s, 1H).

5,6-Diethoxy-7-nitro-benzo[b]thiophene-2-carboxylic acid methyl ester 4,5-Diethoxy-2,3-dinitro-benzaldehyde (1.53 g) was dissolved into N,N-dimethylformamide (6 ml) and then methylthioglycolate (1.36 ml) was added. Triethylamine (2.6 ml) was added in cold to the reaction solution. The mixture was stirred overnight. The solid was filtered and washed with N,N-dimethylformamide.
¹H NMR (DMSO-d₆): δ=1.39 (t, 3H), 1.44 (t, 3H), 4.24 (t, 3H), 4.28 (q, 3H), 8.08 (s, 1H), 8.19 (s, 1H).

5,6-Dihydroxy-7-nitro-benzo[b]thiophene-2-carboxylic acid 5,6-Diethoxy-7-nitro-benzo[b]thiophene-2-carboxylic acid methyl ester (160 mg), hydrobromic acid (8 ml) and acetic acid (8 ml) was refluxed for 6 hours and stirred at room temperature overnight. The solid was filtered and washed with a solution of acetic acid and hydrobromic acid (1:1) and water. The product was recrystallized from acetonitrile.
Yield: 90 mg
¹H NMR (DMSO-d₆): δ=7.71 (s, 1H), 8.05 (s, 1H), 10-11 (br, 2H), 13-13.5 (br, 1H).

Example 18

5,6-Dihydroxy-7-nitro-benzofuran-2-carboxylic acid 2,4-Dihydroxy-5-methoxybenzaldehyde 2,4,5-Trimethoxybenzaldehyde (20 g) was dissolved in dichloromethane (20 ml) and aluminum chloride (34.1 g) was added in small portions. The resulting mixture was stirred at room temperature for 5 hours and then poured in acidic ice water. The dichloromethane layer was separated and the water phase extracted with ethyl acetate. The combined organic layers were extracted with 1 N NaOH. The water phase was acidified with HCl and the precipitate was filtered. The product was recrystallized from toluene.
¹H NMR (400 MHz, DMSO-d₆): δ=3.74 (s, 3H), 6.41 (s, 1H), 7.12 (s, 1H), 9.96 (s, 1H), 10.4 (br, 1H), 10.52 (br, 1H).

4-Benzyloxy-2-hydroxy-5-methoxybenzaldehyde 2,4-Dihydroxy-5-methoxybenzaldehyde (6.0 g), benzyl bromide (9.7 g) and 1,8-diazabicyclo[5.4.0]undec-7-ene (8.6 g) in N,N-dimethylformamide (30 ml) were heated at 100° C. under nitrogen for 5 hours. After cooling to room temperature, 1 N NaOH was added and the mixture washed with ethyl acetate. The water phase was acidified with HCl and the precipitate was filtered.
¹H NMR (400 MHz, DMSO-d₆): δ=3.74 (s, 3H), 5.16 (s, 2H), 6.65 (s, 1H), 7.17 (s, 1H), 7.36-7.47 (m, 5H), 10.02 (s, 1H), 10.68 (s, 1H).

(5-Benzyloxy-2-formyl-4-methoxyphenoxy)acetic acid ethyl ester

4-Benzyloxy-2-hydroxy-5-methoxybenzaldehyde (2.9 g), ethyl bromoacetate (2.3 g) and 1,8-diazabicyclo[5.4.0]undec-7-ene (2.1 g) in N,N-dimethylformamide (30 ml) were heated at 100° C. under nitrogen for 5 hours. After cooling to room temperature, water was added and the mixture extracted with ethyl acetate. Ethyl acetate was washed with 1 N NaOH and 1 N HCl, dried with $Na_2SO_4$ and evaporated to dryness.
¹H NMR (400 MHz, DMSO-d₆): δ=1.20 (t, 3H, J 7.2 Hz), 3.76 (s, 3H), 4.15 (q, 2H, J 7.2 Hz), 4.98 (s, 2H), 5.21 (s, 2H), 6.97 (s, 1H), 7.19 (s, 1H), 7.36-7.47 (m, 5H), 10.29 (s, 1H).

6-Benzyloxy-5-methoxybenzofuran-2-carboxylic acid ethyl ester (5-Benzyloxy-2-formyl-4-methoxyphenoxy)acetic acid ethyl ester (1.5 g), 1,8-diazabicyclo[5.4.0]undec-7-ene (0.33 g) and acetic acid (0.026 g) in N,N-dimethylformamide (8 ml) were stirred at 100° C. under nitrogen for 5 hours. After cooling to room temperature the mixture was poured in ice water and the precipitate was filtered.
¹H NMR (400 MHz, DMSO-d₆): δ=1.32 (t, 3H, J 7.1 Hz), 3.82 (s, 3H), 4.37 (q, 2H, J 7.1 Hz), 5.18 (s, 2H), 7.25 (s, 1H), 7.33-7.50 (m, 6H), 7.62 (d, 1H, J 0.8 Hz).

6-Hydroxy-5-methoxy-benzofuran-2-carboxylic acid ethyl ester

6-Benzyloxy-5-methoxybenzofuran-2-carboxylic acid ethyl ester (7.3 g), acetic acid (45 ml) and conc. HCl (24 ml) were stirred at 50° C. for 0.5 hour. Water was added and pH adjusted to 3 with NaOH. The mixture was extracted with ethyl acetate. Ethyl acetate was dried with $Na_2SO_4$ and evaporated to dryness. The product was recrystallized from toluene.
¹H NMR (400 MHz, DMSO-d₆): δ=1.32 (t, 3H, J 7.1 Hz), 3.82 (s, 3H), 4.31 (q, 2H, J 7.1 Hz), 7.07 (d, 1H, J 0.9 Hz), 7.20 (s, 1H), 7.58 (d, 1H, J 0.9 Hz).

6-Hydroxy-5-methoxy-7-nitro-benzofuran-2-carboxylic acid ethyl ester

6-Hydroxy-5-methoxybenzofuran-2-carboxylic acid ethyl ester (1.5 g) was dissolved to dichloromethane (30 ml) and the solution cooled to −20° C. 1 M $HNO_3$ in dichloromethane (6.4 ml) was added and after 10 minutes the mixture poured in ice water. The dichloromethane layer was separated and the water phase extracted with ethyl acetate. The combined organic phases were dried with $Na_2SO_4$ and evaporated to dryness.

¹H NMR (400 MHz, DMSO-d₆): δ=1.33 (t, 3H, 37.1 Hz), 3.94 (s, 3H, 4.35 (q, 2H, J 7.1 Hz), 7.57 (s, 1H), 7.74 (s, 1H), 11.3 (br, 1H).

5,6-Dihydroxy-7-nitro-benzofuran-2-carboxylic acid

6-Hydroxy-5-methoxy-7-nitro-benzofuran-2-carboxylic acid ethyl ester (0.25 g) was dissolved to dichloromethane and cooled to −5° C. 1 M boron tribromide solution in dichloromethane (4.5 ml) was added and the mixture stirred at 0° C. for 24 hours. The mixture was poured in ice water and the dichloromethane layer separated. The water phase was extracted with ethyl acetate. The combined organic phases were dried with Na₂SO₄ and evaporated to dryness. The product was purified by reverse phase column chromatography using methanol (1%) in dichloromethane as an eluent.

¹H NMR (400 MHz, CD₃OD): δ=7.37 (s, 1H), 7.53 (s, 1H).

Example 19

5,6-Dihydroxy-2-methyl-7-nitro-benzo[d]isothiazol-3-one

2-Mercapto-4,5-dimethoxybenzoic acid

To a solution of 2-amino-4,5-dimethoxybenzoic acid (10.2 g) in HCl (9 ml cons. HCl and 30 ml water) was added a solution of NaNO₂ (3.6 g in 20 ml of water) at 5° C. and stirred for 2 hours. The diazonium solution was filtered and the filtrate was added to a cold solution of Na₂S₂ prepared from sodium sulphide nonahydrate (11.6 g in 20 ml of water) and sulphur (1.5 g) in NaOH solution (1.8 g in 20 ml of water). The mixture was stirred at room temperature overnight, filtered and acidified with concentrated HCl. The precipitate was filtered. The product was a mixture of 2-mercapto-4,5-dimethoxy-benzoic acid and dimerized product 4,4',5,5'-tetramethoxy-2,2'-dithiobis(benzoic acid) and was used for next step without purification.

¹H NMR (400 MHz, DMSO-d₆): δ=monomer 3.65 (s, 3H), 3.72 (s, 3H), 7.29 (s, 1H), 7.36 (s, 1H), dimerized product 3.59 (s, 6H), 3.78 (s, 6H), 7.24 (s, 2H), 7.48 (s, 2H).

2-Chlorosulfenyl-4,5-dimethoxybenzoyl chloride

2-Mercapto-4,5-dimethoxybenzoic acid (12.8 g), toluene (50 ml) and thionyl chloride (100 ml) were heated at 80° C. for 3 hours. The solvent and excess SOCl₂ were evaporated. Toluene was added to the residue and the mixture was evaporated again to dryness. The residue was suspended in toluene (50 ml), sulfuryl chloride (14.3 ml) was added, and the mixture heated at 65° C. for 2 hours. The mixture was evaporated to dryness and the residue used for next step without purification.

¹H NMR (400 MHz, DMSO-d₆): δ=3.84 (s, 3H), 3.89 (s, 3H), 7.32 (s, 1H), 7.79 (s, 1H).

5,6-Dimethoxy-2-methylbenzo[d]isothiazol-3-one

2-Chlorosulfenyl-4,5-dimethoxybenzoyl chloride (5.0 g) was dissolved in pyridine (30 ml) and methylamine hydrochloride (6.0 g) was added. The mixture was stirred at room temperature for 2 days. Ethyl acetate was added and the mixture was washed with 1 N HCl and water. Ethyl acetate was dried with Na₂SO₄ and evaporated to dryness. The crude product was purified by flash chromatography eluting with heptane-ethyl acetate (1:9).

¹H NMR (400 MHz, DMSO-d₆): δ=3.30 (s, 3H), 3.83 (s, 3H), 3.85 (s, 3H), 7.26 (s, 1H), 7.53 (s, 1H).

5,6-Dihydroxy-2-methylbenzo[d]isothiazol-3-one

To a suspension of 5,6-dimethoxy-2-methylbenzo[d]isothiazol-3-one (0.35 g) in dichloromethane (30 ml) boron tribromide (3.1 ml, 1 M solution in dichloromethane) was added at −40° C. The mixture was allowed to warm to −10° C. Next day methanol (30 ml) was added and the mixture was evaporated to dryness. To the residue sodium sulfite solution (9 ml, 5% in water) and brine (9 ml) were added. After stirring at 0° C. the precipitate was filtered.

¹H NMR (400 MHz, DMSO-d₆): δ=3.24 (s, 3H), 7.13 (s, 1H), 7.20 (s, 3H), 9.53 (br, 1H), 10.0 (br, 1H).

Acetic acid 6-acetoxy-2-methyl-3-oxo-2,3-dihydro-benzo[d]isothiazol-5-yl ester 5,6-Dihydroxy-2-methylbenzo[d]isothiazol-3-one (0.23 g) was suspended in N,N-dimethylformamide and triethylamine (0.47 g) and acetic acid anhydride (0.24 g) were added at 0° C. After stirring at room temperature for one hour the mixture was poured to ice water and the precipitate was filtered.

¹H NMR (400 MHz, DMSO-d₆): δ=2.31 (s, 3H), 2.34 (s, 3H), 3.35 (s, 3H), 7.76 (s, 1H), 7.94 (s, 1H).

Acetic acid 6-hydroxy-2-methyl-3-oxo-2,3-dihydro-benzo[d]isothiazol-5-yl ester

To a solution of acetic acid 6-acetoxy-2-methyl-3-oxo-2,3-dihydro-benzo[d]isothiazol-5-yl ester (0.21 g) in dimethylformamide morpholine (0.070 g) was added at 0° C. The mixture was stirred at 0° C. for one hour and then poured to ice water. The precipitated product was filtered.

¹H NMR (400 MHz, DMSO-d₆): δ=2.27 (s, 3H), 3.27 (s, 3H), 7.44 (s, 1H), 7.47 (s, 1H), 10.72 (s, 1H).

Acetic acid 6-hydroxy-2-methyl-7-nitro-3-oxo-2,3-dihydro-benzo[d]isothiazol-5-yl ester To a solution of acetic acid 6-hydroxy-2-methyl-3-oxo-2,3-dihydro-benzo[d]isothiazol-5-yl ester (0.055 g) in acetic acid at 10° C. nitric acid (100% 0.015 g) was added and stirring was continued at room temperature for 15 minutes. The mixture was poured into ice water and extracted with ethyl acetate. Ethyl acetate was dried and evaporated to dryness.

¹H NMR (400 MHz, DMSO-d₆): δ=2.29 (s, 3H), 3.29 (s, 3H), 7.73 (s, 1H).

5,6-Dihydroxy-2-methyl-7-nitro-benzo[d]isothiazol-3-one

Acetic acid 6-hydroxy-2-methyl-7-nitro-3-oxo-2,3-dihydro-benzo[d]isothiazol-5-yl ester (0.046 g) in methanol-HCl (14:1, 7 ml) was heated at 60° C. for 3 hours. The mixture was evaporated to dryness. The crude product was purified by flash chromatography using ethyl acetate as an eluent and followed by crystallization from isopropanol-methanol.

¹H NMR (400 MHz, DMSO-d₆): δ=3.30 (s, 3H), 7.49 (s, 1H).

Example 20

(5,6-Dihydroxy-3-methyl-7-nitro-benzo[b]thiophen-2-yl)morpholin-4-yl-methanone

(5,6-Dimethoxy-3-methylbenzo[b]thiophen-2-yl)morpholin-4-yl-methanone (3-Chloro-5,6-dimethoxybenzo[b]thiophen-2-yl)morpholin-4-yl-methanone (3.0 g) from Example 8, trimethylaluminum (3.2 g) and [1,3-bis(diphenylphosphino)propane]dichloronickel (II) (1.2 g) in 1,2-dimethoxyethane (100 ml) were refluxed under argon for 10 hours. To the cold mixture ethanol (50 ml), water and HCl were added respectively and the mixture was extracted with ethyl acetate. Ethyl acetate was dried and evaporated to dryness. The crude product was purified by flash chromatography eluting with heptane-ethyl acetate (5:5).

$^1$H NMR (400 MHz, DMSO-$d_6$): δ=2.34 (s, 3H), 3.52 (br, 4H), 3.61 (br, 4H), 3.83 (s, 3H), 3.85 (s, 3H), 7.26 (s, 1H), 7.54 (s, 1H).

(5,6-Dihydroxy-3-methylbenzo[b]thiophen-2-yl)morpholin-4-yl-methanone

To a solution of (5,6-dimethoxy-3-methylbenzo[b]thiophen-2-yl)morpholin-4-yl-methanone (0.80 g) in dichloromethane (8 ml) boron tribromide (5.2 ml, 2 M solution in dichloromethane) was added at 0° C. The mixture was allowed to warm to room temperature. After 2 hours at room temperature methanol (16 ml) was added and solvents were evaporated. To the residue sodium sulfite solution (16 ml, 5% in water) was added and after stirring for 0.5 hour the precipitate was filtered.

$^1$H NMR (400 MHz, DMSO-$d_6$): δ=2.24 (s, 3H), 3.51 (br, 4H), 3.59 (br, 4H), 7.07 (s, 1H), 7.21 (s, 1H), 9.20 (s, 1H), 9.42 (s, 1H).

(5,6-Dihydroxy-3-methyl-7-nitro-benzo[b]thiophen-2-yl)morpholin-4-yl-methanone (5,6-Dihydroxy-3-methylbenzo[b]thiophen-2-yl)morpholin-4-yl-methanone (0.10 g) was dissolved to ethyl acetate (60 ml). Nitric acid (2 eq, 2 M solution in dichloromethane) was added in small portions at 55° C. 15 minutes after last addition the mixture was cooled, washed with water, dried with $Na_2SO_4$ and concentrated to small volume. The precipitated product was filtered.

$^1$H NMR (400 MHz, DMSO-$d_6$): δ=2.31 (s, 3H), 3.53 (br, 4H), 3.61 (br, 4H), 7.54 (s, 1H), 10.5 (br, 2H).

Example 21

5,6-Dihydroxy-7-nitro-benzo[b]thiophene-2-carboxylic acid ethyl ester

5,6-Dihydroxy-7-nitro-benzo[b]thiophene-2-carboxylic acid ethyl ester 5,6-Dihydroxy-7-nitro-benzo[b]thiophene-2-carboxylic acid (50 mg, 0.20 mmol) from Example 17 and thionyl chloride (130 µl) in ethanol (2 ml) were refluxed for 1.5 hours, evaporated to dryness and recrystallized from ethanol.
Yield: 46 mg
$^1$H NMR (DMSO-$d_6$): δ=8.13 (1H, s), 7.72 (1H, s), 4.34 (2H, q), 1.34 (3H, t).

Example 22

5,6-Dihydroxy-4-nitro-isobenzofuran-1,3-dione

5,6-Dimethoxy-3H-isobenzofuran-1-one

A mixture of 3,4-dimethoxy-benzoic acid (10 g) in 37% HCl (150 ml) and formaldehyde (25 ml, 37 wt. % solution in water) was heated to 90° C. for 4¾ hours, and then insoluble material was removed by filtration. The filtrate was quenched with water (200 ml) and extracted three times with ethyl acetate (200 ml). The combined organic layers were washed with aqueous NaOH (40 ml, 2.5 M) and water (100 ml). The organic solvent was dried over anhydrous $Na_2SO_4$, filtered and evaporated to dryness
Yield: 8.9 g
$^1$H NMR (DMSO-$d_6$): δ=7.27 (1H, s), 7.24 (1H, s), 5.28 (2H, s), 3.88 (3H, s), 3.84 (3H, s).

4,5-Dimethoxy-phthalic acid

To a mixture of 5,6-dimethoxy-3H-isobenzofuran-1-one (4.5 g) and 7% aqueous NaOH (47 ml) was added $KMnO_4$ (4.0 g) diluted in water (125 ml). The mixture was stirred at room temperature for 4 days. Insoluble material was removed by filtration. The filtrate was cooled with ice-water bath and acidified with concentrated HCl. The acidic solution was extracted three times with ethyl acetate (300 ml). The combined organic layers were dried over anhydrous $Na_2SO_4$ and evaporated.
Yield: 4.8 g
$^1$H NMR (DMSO-$d_6$): δ=7.19 (2H, s), 3.83 (6H, s).

5,6-Dimethoxy-4-nitro-isobenzofuran-1,3-dione 4,5-Dimethoxy-phthalic acid (1.0 g) was cooled in ice-water bath. A cooled mixture of sulfuric acid (3.0 ml) and fuming nitric acid (3.0 ml) was added dropwise. The mixture was stirred for 10 minutes and left standing for 10 minutes. A mixture of brine and ice was added (1:1). The solid was filtered off, washed with water and recrystallized from ethanol.
Yield: 0.46 g
$^1$H NMR (DMSO-$d_6$): δ=8.19 (1H, s), 4.11 (3H, s), 4.05 (3H, s).

5-Hydroxy-6-methoxy-4-nitro-isobenzofuran-1,3-dione 5,6-Dimethoxy-4-nitro-isobenzofuran-1,3-dione (346 mg), 48% hydrogen bromide (1.5 ml), Acetic acid (15 ml) and benzyl triethylammonium bromide (37 mg) were heated at 140° C. for 3 hours. The acetic acid and water was removed in vacuo. The remainder was filtered through silica gel using a mixture of toluene, ethyl acetate and methanol (8:1:1) as eluent. Appropriate fractions were collected and evaporated.
Yield: 275 mg
$^1$H NMR (DMSO-$d_6$): δ=7.44 (1H, s), 3.85 (3H, s).

5,6-Dihydroxy-4-nitro-isobenzofuran-1,3-dione

5-Hydroxy-6-methoxy-4-nitro-isobenzofuran-1,3-dione (115 mg), aluminum chloride (80 mg) was mixed with ethyl acetate (3 ml). Pyridine (155 µl) in ethyl acetate (2 ml) was added dropwise. The resulting mixture was stirred at room temperature for 0.5 hours, heated to reflux for 3 hours, and then quenched with water (0.5 ml) and conc. HCl (0.5 ml) at 60° C. Ethyl acetate and water was removed in vacuo. The remainder was mixed with brine (2 ml) and extracted two times with ethyl acetate (15 ml). The combined organic layers were dried over anhydrous $Na_2SO_4$, filtrated, evaporated and triturated with diethyl ether.

Yield: 55 mg $^1H$ NMR (DMSO-$d_6$): δ=7.42 (1H, s).

Example 23

5,6-Dihydroxy-4-nitro-3H-isobenzofuran-1-one 5,6-Dihydroxy-3H-isobenzofuran-1-one 5,6-Dimethoxy-3H-isobenzofuran-1-one (2.91 g) was dissolved in dichloromethane (150 ml) followed by cooling to −50° C. Boron tribromide (34.9 ml, 1.0M solution in dichloromethane) was added dropwise under nitrogen atmosphere. The mixture was slowly allowed to warn overnight to room temperature and continued stirring for 3 hours. The reaction was quenched with methanol followed by evaporation to dryness. The remainder was mixed with 5% aqueous $Na_2SO_3$ (20 ml) and brine (20 ml) and filtrated.

Yield: 2.31 g $^1H$ NMR (DMSO-$d_6$): δ 10.22 (1H, bs), 9.70 (1H, bs), 7.09 (1H, s), 6.93 (1H, s), 5.17 (2H, s).

Acetic acid 6-acetoxy-3-oxo-1,3-dihydro-isobenzofuran-5-yl ester (8)

5,6-Dihydroxy-3H-isobenzofuran-1-one (2.26 g), acetic anhydride (25 ml) and pyridine (2.31 ml) were stirred for 5 hours at room temperature. Acetic anhydride was removed in vacuo and the remainder was mixed with water (20 ml), filtrated and washed with water. Yield: 3.35 g $^1H$ NMR (DMSO-$d_6$): δ=7.81 (1H, s), 7.64 (1H, s), 5.42 (2H, s), 2.34 (3H, s), 2.32 (3H, s).

Acetic acid 6-hydroxy-3-oxo-1,3-dihydro-isobenzofuran-5-yl ester

Acetic acid 6-acetoxy-3-oxo-1,3-dihydro-isobenzofuran-5-yl ester (5.0 g) was dissolved in N,N-dimethylformamide (100 ml) followed by addition of morpholine (1.78 ml). The solution was stirred at room temperature overnight followed by concentration in reduced pressure. Ethyl acetate (200 ml) was added to the remainder. The organic phase was washed two times with a mixture of aqueous HCl (50 ml, 2M) and brine (50 ml). The organic solvent was dried over anhydrous $Na_2SO_4$, filtered and evaporated to dryness.

Yield: 3.96 g $^1H$ NMR (DMSO-$d_6$): δ 11.01 (1H, bs), 7.51 (1H, s), 7.12 (1H, s), 5.29 (2H, s), 2.28 (3H, s).

Acetic acid 6-hydroxy-7-nitro-3-oxo-1,3-dihydro-isobenzofuran-5-yl ester

Acetic acid 6-hydroxy-3-oxo-1,3-dihydro-isobenzofuran-5-yl ester (3.8 g) was mixed with acetic acid (150 ml) followed by addition of 65% nitric acid (2.5 ml). After dissolution the mixture was stirred at room temperature for 2 hours followed by removal of the acetic acid and water in vacuo. The remainder was filtered through silica gel using a mixture of toluene, ethyl acetate and methanol (8:1:1) as eluent. Appropriate fractions were collected and evaporated to dryness.

Yield: 4.1 g $^1H$ NMR (DMSO-$d_6$): δ=7.91 (1H, s), 5.59 (2H, s), 2.33 (3H, s).

5,6-Dihydroxy-4-nitro-3H-isobenzofuran-1-one

Acetic acid 6-hydroxy-7-nitro-3-oxo-1,3-dihydro-isobenzofuran-5-yl ester (4.1 g) was suspended in methanol (150 ml) and 37% HCl (20 ml) followed by stirring at room temperature for 3 days. The precipitate was filtered and washed with methanol.

Yield: 2.25 g $^1H$ NMR (DMSO-$d_6$): δ=7.32 (1H, s), 5.50 (2H, s).

Example 24

5,6-Dihydroxy-4,7-dinitro-3H-isobenzofuran-1-one 5,6-Dimethoxy-4,7-dinitro-3H-isobenzofuran-1-one 5,6-Dimethoxy-3H-isobenzofuran-1-one (582 mg) was cooled in ice-water bath. A cooled mixture of sulfuric acid (2 ml) and fuming nitric acid (2 ml) was added dropwise. The mixture was stirred for 15 minutes and left standing for 45 minutes. The reaction was quenched with ice. The aqueous phase was extracted three times with ethyl acetate (30 ml) and washed with brine (15 ml). The organic solvent was dried over anhydrous $Na_2SO_4$, filtered and evaporated to dryness.

Yield: 586 mg $^1H$ NMR (DMSO-$d_6$): δ=5.67 (2H, s), 4.12 (3H, s), 4.00 (3H, s).

5-Hydroxy-6-methoxy-4,7-dinitro-3H-isobenzofuran-1-one 5,6-Dimethoxy-4,7-dinitro-3H-isobenzofuran-1-one (450 mg), acetic acid (15 ml) and 37% aqueous HCl (3 ml) were refluxed for 7.25 hours. The acetic acid and water were evaporated in vacuo. The residue was purified by column chromatography (toluene-ethyl acetate-methanol 8:1:1).

Yield: 215 mg $^1H$ NMR (DMSO-$d_6$): δ 5.48 (2H, s), 3.86 (3H, s).

5,6-Dihydroxy-4,7-dinitro-3H-isobenzofuran-1-one

5-Hydroxy-6-methoxy-4,7-dinitro-3H-isobenzofuran-1-one (210 mg) was dissolved in ethyl acetate (2.5 ml) followed by addition of aluminum chloride (132 mg) in nitrogen atmosphere. Pyridine (265 μl, 3.28 mmol) was added dropwise. The resulting mixture was heated to reflux for 2 hours, and then quenched with water (0.5 ml) and conc. HCl (0.5 ml) at 75° C. Ethyl acetate (15 ml) was added and phases were separated. The aqueous layer was extracted once with ethyl acetate (15 ml). The combined organic layers were dried over anhydrous $Na_2SO_4$. The product was filtrated, evaporated to dryness and recrystallized from heptane-toluene-ethyl acetate.

Yield: 76 mg $^1H$ NMR (DMSO-$d_6$): δ 5.41 (2H, s).

Example 25

7-Nitro-2-phenyl-benzothiazole-5,6-diol

Catechol Cyclohexylidene Ketal

Catechol (55 g), cyclohexanone (65 ml), p-toluenesulfonic acid monohydrate (0.50 ml) and toluene (500 ml) were refluxed at Dean-Stark apparatus for 4.5 hours. The reaction mixture was washed with NaOH-solution and water, dried and evaporated to dryness.

Yield: 90 g $^1$H NMR (DMSO-$d_6$): δ 1.46 (m, 2H), 1.65 (m, 4H), 1.85 (t, 4H, J 6.2), 6.75-6.85 (m, 4H)

4-Nitrocatechol cyclohexylidene ketal

To a solution of catechol cyclohexylidene ketal (87.3 g) in methylene chloride (900 ml) was added a solution of nitric acid in methylene chloride (2 M, 250 ml) at a rate to keep the temperature at about 25° C. with the use of a water bath. The product mixture was washed with sodium hydroxide (1 M, 500 ml). The organic phase was separated, dried and evaporated.

Yield: 106 g $^1$H NMR (DMSO-$d_6$): δ=1.49 (m, 2H), 1.67 (m, 4H), 1.95 (t, 4H, J 6.2), 7.08 (d, 1H, J 8.8 Hz), 7.70 (d, 1H, J 2.4 Hz), 7.86 (dd, 1H, J 2.4 and 8.8).

4-Aminocatechol cyclohexylidene ketal

4-Nitrocatechol cyclohexylidene ketal (2 g) was hydrogenated in ethyl acetate (12 ml) with Pd—C (0.2 g) as a catalyst.

Yield: 1.77 g $^1$H NMR (DMSO-$d_6$): δ=1.45 (m, 2H), 1.60 (m, 4H), 1.79 (m, 4H), 4.62 (br, 2H), 5.94 (dd, 1H, J 3.1 and 12.2 Hz), 6.14 (d, 1H, J 3.1), 6.48 (d, 1H, J 12.2 Hz).

2-Phenyl-benzothiazole-5,6-diol cyclohexylidene ketal

4-Aminocatechol cyclohexylidene ketal (1.77 g), benzaldehyde (0.82 ml) and sulfur (0.55 g) were refluxed in dimethyl acetamide (8.6 ml) for two hours. The reaction mixture was poured into water (100 ml) and extracted with ether (100 ml), dried, evaporated and recrystallized from acetonitrile.

Yield: 0.93 g $^1$H NMR (DMSO-$d_6$): δ=1.49 (m, 2H), 1.69 (m, 4H), 1.94 (m, 4H), 7.50-7.57 (m, 5H), 7.99-8.01 (m, 2H).

7-Nitro-2-phenyl-benzothiazole-5,6-diol cyclohexylidene ketal

To a solution of the 2-phenyl-benzothiazole-5,6-diol cyclohexylidene ketal (0.93 g) in acetic acid (25 ml) was added concentrated nitric acid (1.5 ml). The reaction mixture was filtered. Water was added to the filtrate and the precipitate was filtered. The latter product was recrystallized from acetonitrile.

Yield: 0.40 g $^1$H NMR (DMSO-$d_6$): δ=1.57 (m, 2H), 1.75 (m, 4H), 2.10 (m, 4H), 7.58-7.60 (m, 3H), 7.99 (s, 1H), 8.09-8.11 (m, 2H).

7-Nitro-2-phenyl-benzothiazole-5,6-diol

7-Nitro-2-phenyl-benzothiazole-5,6-diol cyclohexylidene ketal (0.35 g), acetic acid (8.8 ml) and concentrated hydrochloric acid (3.5 ml) were refluxed for two hours. The product was filtered and washed with acetic acid.

Yield: 0.27 g

Melting point: 221-224° C.

$^1$H NMR (DMSO-$d_6$): δ=7.55-7.58 (m, 3H), 7.79 (s, 1H), 8.07-8.09 (m, 2H), 10.6 (br, 2H).

Example 26

6,7-Dihydroxy-5-nitro-benzo[b]thiophene-2-carboxylic acid methyl ester

4-Hydroxy-3-methoxy-5-nitrobenzaldehyde

To a solution of concentrated nitric acid (900 ml) and water (900 ml) was added 4-hydroxy-3-methoxybenzaldehyde (300 g) at a temperature under 10° C. After stirring 1 hour at 0° C. the precipitate was filtered and washed with water.

$^1$H NMR (DMSO-$d_6$): δ=3.90 (s, 3H), 7.64 (d, 1H, J 1.8 Hz), 8.09 (d, 1H, J 1.8 Hz), 9.88 (s, 1H).

2-Bromo-3,4-dihydroxy-5-nitrobenzaldehyde

The product of the previous reaction step, concentrated hydrobromic acid (2 l) and acetic acid (2 l) were refluxed for 2 days. Water (1 l) and saturated $Na_2SO_4$-solution (1 l) were added and the mixture was extracted with ether. The organic phase was dried with $Na_2SO_4$ and evaporated to small volume. The precipitated product was filtered.

$^1$H NMR (DMSO-$d_6$): δ=7.92 (s, 1H), 10.3 (s, 1H).

2-Bromo-3,4-diethoxy-5-nitrobenzaldehyde

2-Bromo-3,4-dihydroxy-5-nitrobenzaldehyde (5.2 g), ethylbromide (4.5 ml) and N,N-diisopropylethylamine (10.5 ml) in N,N-dimethylformamide (50 ml) were stirred at 70° C. for 2 days. The mixture was poured into water and extracted with ether. The organic phase was washed with NaOH-solution, dried with $Na_2SO_4$ and evaporated to dryness.

$^1$H NMR (DMSO-$d_6$): δ=1.33 (t, 3H, J 8.0 Hz), 1.40 (t, 3H, J 8.0 Hz), 4.15 (q, 2H, 8.0 Hz), 4.30 (q, 2H, J 8.0 Hz), 8.09 (s, 1H), 10.2 (s, 1H).

6,7-Diethoxy-5-nitro-benzo[b]thiophene-2-carboxylic acid methyl ester

To a solution of 2-bromo-3,4-diethoxy-5-nitrobenzaldehyde (1.5 g) in N,N-dimethylformamide (5 ml) were added methyl thioglycolate (1.5 g) and triethylamine (2.2 ml) at 0° C. Stirring was continued at room temperature overnight. 1 M HCl was added and the product was extracted with ether. The organic phase was dried with $Na_2SO_4$ and evaporated. The crude product was triturated with methanol.

$^1$H NMR (DMSO-$d_6$): δ=1.34 (t, 3H, J 7.8 Hz), 1.39 (t, 3H, J 7.8 Hz), 3.92 (s, 3H), 4.22 (q, 2H, J 7.8 Hz), 4.31 (q, 2H, J 7.8 Hz), 8.30 (s, 1H), 8.82 (s, 1H).

6,7-Dihydroxy-5-nitro-benzo[b]thiophene-2-carboxylic acid methyl ester 6,7-Diethoxy-5-nitro-benzo[b]thiophene-2-carboxylic acid methyl ester (0.77 g), zinc chloride (5.0 g) and conc. HCl (1.3 ml) were mixed and heated at 100° C. for 2 hours. The reaction mixture was cooled. Water (20 ml) was added and the precipitate was filtered. The crude product was recrystallized twice from methanol.

Melting point: 216-218° C.

$^1$H NMR (DMSO-$d_6$): δ=3.84 (s, 3H), 8.17 (s, 1H), 8.21 (s, 1H), 10.2 (br, 2H).

Example 27

1-(5,6-Dimethoxy-7-nitro-benzo[b]thiophen-2-yl)-nonan-1-one

1-(5,6-Dimethoxy-7-nitro-benzo[b]thiophen-2-yl)-nonan-1-one 5,6-Dihydroxy-7-nitro-benzo[b]thiophene-2-carboxylic acid (0.1 g) from Example 17, 1-octanol (2 ml) and concentrated sulphuric acid (one drop) were refluxed at 120° C. for 3 hours. The product was purified by column chromatography using toluene-ethyl acetate-acetic acid 8:1:1 as the eluent.

Melting point: 115-117° C.
Yield: 62.4 mg
$^1$H NMR (DMSO-$d_6$): δ=0.83-0.87 (m, 3H), 1.26-1.39 (m, 10H), 1.68-1.73 (m, 2H), 4.26-4.30 (q, 2H), 7.69 (s, 1H), 8.11 (s, 1H).

Example 28

(3-Chloro-5,6-dihydroxy-4,7-dinitro-benzo[b]thiophen-2-yl)-morpholin-4-yl-methanone

(3-Chloro-5,6-dihydroxy-benzo[b]thiophen-2-yl)-morpholin-4-yl-methanone

Aluminum chloride (6.62 g) was gradually added into cool acetonitrile (14.7 ml) at 10° C. and then sodium iodide (5.57 g) was added. The solution was stirred at room temperature 30 min. (3-Chloro-5,6-dimethoxy-benzo[b]thiophen-2-yl)-morpholin-4-yl-methanone (2.1 g) from Example 8 was added. The solution was stirred at 50° C. five hours and at room temperature overnight. 2N HCl (8.4 ml) was added into the cool reaction solution and then sodium sulfite (1.58 g) and water (35 ml) were added. The mixture was stirred at 40° C. 30 min. The product was filtered, washed with water and dried in vacuum.

$^1$H NMR (DMSO-$d_6$): δ=3.52 (m, 4H), 3.63 (m, 4H), 7.11 (1H), 7.32 (1H), 9.63 (1H), 9.70 (1H).

(3-Chloro-5,6-dihydroxy-4,7-dinitro-benzo[b]thiophen-2-yl)-morpholin-4-yl-methanone (3-Chloro-5,6-dihydroxy-benzo[b]thiophen-2-yl)-morpholin-4-yl-methanone (1.0 g) was slurried in methanesulfonic acid (20 ml) and then was gradually added potassium nitrate (0.73 g). The reaction mixture was stirred at room temperature and after 15 min it was poured into ice water (100 ml). The product was filtered, washed with water and methanol and dried in vacuum.

Melting point: 233-235° C.
$^1$H NMR (DMSO-$d_6$): δ=3.52 (m, 4H), 3.62 (m, 4H), 9.6-10.4 (br, 2H).

Example 29

(3,4-Chloro-5,6-dihydroxy-7-dinitro-benzo[b]thiophen-2-yl)-morpholin-4-yl-methanone

(3,4-Chloro-5,6-dihydroxy-7-dinitro-benzo[b]thiophen-2-yl)-morpholin-4-yl-methanone (3-Chloro-5,6-dihydroxy-7-dinitro-benzo[b]thiophen-2-yl)-morpholin-4-yl-methanone (0.5 g) from Example 8, copper(II) chloride (0.9 g) and lithium chloride (0.3 g) in acetic acid (5 ml) were refluxed for five hours. Water was added to the reaction mixture. The resultant solid was filtered, washed with water and dried in vacuum.

Melting point: 273-279° C.
$^1$H NMR (DMSO-$d_6$): δ=3.64 (m, 8H), 8.8-10.8 (br, 2H).

Example 30

(3-Chloro-5,6-dihydroxy-4-nitro-benzo[b]thiophen-2-yl)-morpholin-4-yl-methanone

(3-Chloro-5,6-dihydroxy-4-nitro-benzo[b]thiophen-2-yl)-morpholin-4-yl-methanone (3-Chloro-5,6-dihydroxy-benzo[b]thiophen-2-yl)-morpholin-4-yl-methanone (2.0 g) from Example 28 was slurried in methanesulfonic acid (40 ml) and then potassium nitrate (0.64 g) was gradually added. The reaction mixture was stirred at room temperature and after 15 min it was poured into ice water (100 ml). The solid was filtered, washed with water (50 ml) and dried in vacuum. The resultant solid was dissolved in DMF (6.2 ml) and then ethanol (18.4 ml) was added. The product was filtered and washed with methanol (15 ml).

Melting point: 216° C.
$^1$H NMR (DMSO-$d_6$): δ=3.43 (m, 4H), 3.62 (m, 4H), 7.59 (s, 1H), 10.55 (b, 1H), 11.21 (br, 1H).

Example 31

(3-Chloro-5,6-dihydroxy-7-nitro-benzo[b]thiophen-2-yl)-(2,6-dimethyl-morpholin-4-yl)-methanone

(3-Chloro-5,6-dimethoxy-benzo[b]thiophen-2-yl)-(2,6-dimethyl-morpholin-4-yl)-methanone 3-Chloro-5,6-dimethoxy-benzo[b]thiophene-2-carbonyl chloride (2.0 g) and 2,6-dimethylmorpholine (1.82 g) was suspended in tetrahydrofuran (15 ml) and triethylamine (0.96 ml) was added and stirring continued at room temperature for weekend. Water was added, pH adjusted to 3 by HCl, and the precipitate filtered.

$^1$H NMR (400 MHz, DMSO-$d_6$): δ=1.10 (s, 6H), 2.6-4.5 (br, 6H), 3.85 (s, 3H), 3.88 (s, 3H), 7.22 (s, 1H), 7.68 (s, 1H).

(3-Chloro-5,6-dihydroxy-benzo[b]thiophen-2-yl)-(2,6-dimethyl-morpholin-4-yl)-methanone Sodium iodide (1.62 g) was added to a solution of aluminum chloride (2.16 g) in acetonitrile (5 ml). After 30 minutes stirring (3-chloro-5,6-dimethoxy-benzo[b]thiophen-2-yl)-(2,6-dimethyl-morpholin-4-yl)-methanone was added and the mixture was heated at 50° C. for 12 hours. To the mixture 2 N HCl (4 ml), $Na_2SO_3$ (0.68 g) and water were added and the mixture was heated at 60° C. for 30 minutes and then cooled to room temperature. The precipitate was filtered.

$^1$H NMR (400 MHz, DMSO-$d_6$): δ=1.09 (s, 6H), 2.6-4.4 (br, 6H), 7.11 (s, 1H), 7.31 (s. 1H), 9.63 (s, 1H), 9.70 (s, 1H).

(3-Chloro-5,6-dihydroxy-7-nitro-benzo[b]thiophen-2-yl)-(2,6-dimethyl-morpholin-4-yl)-methanone (3-Chloro-5,6-dihydroxy-benzo[b]thiophen-2-yl)-(2,6-dimethyl-morpholin-4-yl)-methanone (0.20 g) was dissolved in ethyl acetate and 1 N $HNO_3$ solution in dichloromethane (0.64 ml) was added. Stirring was continued for 4 hours. The mixture was concentrated to smaller volume and the precipitate filtered and washed with water. The crude product was recrystallized from N,N-dimethylformamide/ethanol (25:75).

$^1$H NMR (400 MHz, DMSO-d$_6$): δ=1.09 (s, 6H), 2.6-4.5 (br, 6H), 7.49 (s, 1H).

Example 32

(3-Chloro-5,6-dihydroxy-7-nitro-benzo[b]thiophen-2-yl)-(4-hydroxy-piperidin-1-yl)-methanone (3-Chloro-5,6-dimethoxy-benzo[b]thiophen-2-yl)-(4-hydroxy-piperidin-1-yl)-methanone 3-Chloro-5,6-dimethoxy-benzo[b]thiophene-2-carbonyl chloride (2.0 g) and 4-hydroxy-piperidine (1.60 g) was suspended in tetrahydrofuran (15 ml) and triethylamine (0.96 ml) was added and stirring continued at room temperature for two hours. Water was added, pH adjusted to 3 by HCl and the precipitate filtered.

$^1$H NMR (400 MHz, DMSO-d$_6$): δ=1.38-1.42 (m, 2H), 1.72-1.85 (m, 2H), 3.2-3.3 (m, 2H), 3.4-4.2 (br, 2H) 3.7-3.8 (m, 1H), 3.85 (s, 3H), 3.88 (s, 3H), 4.81 (d, 1H, J=4.1), 7.21 (s, 1H), 7.67 (s, 1H).

(3-Chloro-5,6-dihydroxy-benzo[b]thiophen-2-yl)-(4-hydroxy-piperidin-1-yl)-methanone Sodium iodide (1.62 g) was added to a solution of aluminum chloride (2.52 g) in acetonitrile (7 ml). After 30 minutes stirring (3-chloro-5,6-dimethoxy-benzo[b]thiophen-2-yl)-(4-hydroxy-piperidin-1-yl)-methanone (0.96 g) was added and the mixture was heated at 50° C. for 12 hours. To the mixture 2 N HCl (4 ml), Na$_2$SO$_3$ (0.68 g) and water were added and the mixture was heated at 60° C. for 30 minutes and then cooled to room temperature. The precipitate was filtered.

$^1$H NMR (400 MHz, DMSO-d$_6$): δ=1.35-1.45 (m, 2H), 1.72-1.82 (m, 2H), 3.18-3.30 (m, 2H), 3.4-4.2 (br, 2H), 3.7-3.8 (m, 1H), 4.80 (d, 1H, J=4.1 Hz), 7.10 (s, 1H), 7.31 (s, 1H), 9.61 (s, 1H), 9.68 (s, 1H).

(3-Chloro-5,6-dihydroxy-7-nitro-benzo[b]thiophen-2-yl)-(4-hydroxy-piperidin-1-yl)-methanone A solution of 1 M HNO$_3$ in dichloromethane (0.67 ml) was added to a solution of (3-chloro-5,6-dihydroxy-benzo[b]thiophen-2-yl)-(4-hydroxy-piperidin-1-yl)-methanone (0.17 g) in ethyl acetate (10 ml). Stirring was continued at 60° C. for 3 hours and then at room temperature overnight. The mixture was concentrated to smaller volume and the precipitate filtered and washed with water. The crude product was recrystallized from N,N-dimethylformamide/ethanol (25:75).

$^1$H NMR (400 MHz, DMSO-d$_6$): δ=1.35-1.45 (m, 2H), 1.70-1.85 (br, 2H), 3.1-4.0 (br, 6H), 7.49 (s, 1H).

Example 33

(3-Bromomethyl-5,6-dihydroxy-7-nitro-benzo[b]thiophen-2-yl)-morpholin-4-yl-methanone (3-Bromomethyl-5,6-dimethoxy-benzo[b]thiophen-2-yl)-morpholin-4-yl-methanone (5,6-Dimethoxy-3-methylbenzo[b]thiophen-2-yl)morpholin-4-yl-methanone (2.0 g) from Example 20, N-bromosuccinimide (1.18 g) and 2,2'-azobis(2-methylpropionitrile) (40 mg) in carbon tetrachloride (6 ml) was refluxed under argon for 4 hours. The mixture was cooled and filtered and the filtrate evaporated to dryness. The product was a mixture of (4-bromo-5,6-dimethoxy-3-methyl-benzo[b]thiophen-2-yl)-morpholin-4-yl-methanone and (3-bromomethyl-5,6-dimethoxy-benzo[b]thiophen-2-yl)-morpholin-4-yl-methanone. The compounds were separated by flash chromatography using ethyl acetate/heptane (1:4) as an eluent.

(3-Bromomethyl-5,6-dimethoxy-benzo[b]thiophen-2-yl)-morpholin-4-yl-methanone: $^1$H NMR (400 MHz, DMSO-d$_6$): δ=3.53 (br, 4H), 3.64 (br, 4H), 3.84 (s, 3H), 3.86 (s, 3H), 4.91 (s, 2H), 7.45 (s, 1H), 7.61 (s, 1H).

(4-Bromo-5,6-dimethoxy-3-methyl-benzo[b]thiophen-2-yl)-morpholin-4-yl-methanone: $^1$H NMR (400 MHz, DMSO-d$_6$): δ=2.56 (s, 3H), 3.51 (br, 4H), 3.57 (br, 4H), 3.76 (s, 3H), 3.89 (s, 3H), 7.73 (s, 1H).

(3-Bromomethyl-5,6-dihydroxy-benzo[b]thiophen-2-yl)-morpholin-4-yl-methanone

A solution of 1 N boron tribromide in dichloromethane (3.4 ml) was added to a solution of (3-bromomethyl-5,6-dimethoxy-benzo[b]thiophen-2-yl)-morpholin-4-yl-methanone) (0.46 g) in dichloromethane (10 ml) at −20° C. Stirring was continued at 0° C. for one hour. Methanol was added and the mixture was evaporated to dryness. To the residue 5% Na$_2$SO$_3$ solution (5 ml) was added, the mixture acidified and the precipitate filtered.

$^1$H NMR (400 MHz, DMSO-d$_6$): δ=3.52 (br, 4H), 3.61 (br, 4H), 4.78 (s, 2H), 7.26 (s, 1H), 7.28 (s, 1H), 9.39 (s, 1H), 9.56 (s, 1H).

(3-Bromomethyl-5,6-dihydroxy-7-nitro-benzo[b]thiophen-2-yl)-morpholin-4-yl-methanone A solution of 1 M HNO$_3$ in dichloromethane (1.02 ml) was added to a solution of (3-bromomethyl-5,6-dihydroxy-benzo[b]thiophen-2-yl)-morpholin-4-yl-methanone (0.35 g) in ethyl acetate (50 ml) and stirring continued at 60° C. for 2 hours. The cooled mixture was washed with water, dried and evaporated to dryness. The product was recrystallized from acetone.

$^1$H NMR (400 MHz, CDCl$_3$): δ=3.68 (br, 4H), 3.78 (br, 4H), 4.70 (s, 2H), 5.94 (s, 1H), 7.78 (s, 1H), 11.6 (s, 1H).

Example 34

5,6-Dihydroxy-3-methyl-2-(morpholine-4-carbonyl)-benzo[b]thiophene-4-carbonitrile 5,6-Dimethoxy-3-methyl-2-(morpholine-4-carbonyl)-benzo[b]thiophene-4-carbonitrile (4-Bromo-5,6-dimethoxy-3-methyl-benzo[b]thiophen-2-yl)-morpholin-4-yl-methanone (0.42 g) from Example 33 and copper(I) cyanide (2.0 g) in N,N-dimethylformamide (8 ml) were irradiated in a microwave oven at 150° C. for 1.5 hours. To the mixture water was added and the product was extracted into ethyl acetate. Ethyl acetate was dried and evaporated to dryness.

$^1$H NMR (400 MHz, CDCl$_3$): δ=2.66 (s, 3H), 3.5-3.8 (br, 8H), 3.96 (s, 3H), 4.05 (s, 3H), 7.46 (s, 1H). NOESY NMR indicated the cyano group at the position 4.

5,6-Dihydroxy-3-methyl-2-(morpholine-4-carbonyl)-benzo[b]thiophene-4-carbonitrile A solution of 1 N boron tribromide in dichloromethane (3.4 ml) was added to a solution of 5,6-di(ethoxy-3-methyl-2-

(morpholine-4-carbonyl)-benzo[b]thiophene-4-carbonitrile (0.19 g) in dichloromethane (40 ml) at 0° C. The mixture was allowed to stay at 6° C. for two days. Methanol was added and the mixture was evaporated to dryness. To the residue 0.1 N HCl was added and the product was extracted into ethyl acetate. Ethyl acetate was dried and evaporated to dryness. The compound was recrystallized from isopropanol.

$^1$H NMR (400 MHz, DMSO-d$_6$): δ=2.49 (s, 3H), 3.51 (br, 4H), 3.60 (br, 4H), 7.54 (s, 1H).

Example 35

(3-Chloro-5,6-dihydroxy-7-cyano-benzo[b]thiophen-2-yl)-morpholin-4-yl-methanone (3-Chloro-6-hydroxy-5-methoxy-benzo[b]thiophen-2-yl)-morpholin-4-yl-methanone (3-Chloro-5,6-dimethoxy-benzo[b]thiophen-2-yl)-morpholin-4-yl-methanone (11.8 g) from Example 8 was slurried in dichloromethane (250 ml) and aluminum chloride (33 g) was gradually added. The reaction mixture was stirred at room temperature for 24 hours. Then 6M hydrochloric acid (96 ml) was gradually added. The organic layer was dried with sodium sulphate, evaporated and dried in vacuum. The product was a mixture of two compounds and was used for the next step without any purification.

(7-Bromo-3-chloro-6-hydroxy-5-methoxy-benzo[b]thiophen-2-yl)-morpholin-4-yl-methanone (3-Chloro-6-hydroxy-5-methoxy-benzo[b]thiophen-2-yl)-morpholin-4-yl-methanone (6.9 g) was slurried in acetic acid. A solution of bromine (3.51 g) in acetic acid (31 ml) was gradually added. The reaction mixture was stirred at room temperature and after 15 minutes water (125 ml) was added. The reaction mixture was stirred at cool for 1.5 hours. The solid was filtered and dried in vacuum. The product was a mixture of two compounds and was used for the next step without any purification.

(7-Bromo-3-chloro-5,6-dimethoxy-benzo[b]thiophen-2-yl)-morpholin-4-yl-methanone (7-Bromo-3-chloro-6-hydroxy-5-methoxy-benzo[b]thiophen-2-yl)-morpholin-4-yl-methanone (7.0 g) was dissolved in 1-methyl-2-pyrrolidinone (35 ml) and di-isopropylethylamine was gradually added. The reaction solution was warmed at 80° C. for 3 hours. Then water (350 ml) was added. The reaction solution was stirred at room temperature for 30 minutes. The product was extracted into ethyl acetate. The organic phase was washed with 1M hydrochloric acid and a solution of sodium sulphate, evaporated and dried in vacuum. The product was purified by flash chromatography using heptane-ethyl acetate as an eluent.

$^1$H NMR (DMSO-d$_6$): δ=3.46 (br, 4H), 3.64 (br, 4H), 3.84 (s, 3H), 3.97 (s, 3H), 7.39 (s, 1H).

(3-Chloro-7-cyano-5,6-dimethoxy-benzo[b]thiophen-2-yl)-morpholin-4-yl-methanone (7-Bromo-3-chloro-5,6-dimethoxy-benzo[b]thiophen-2-yl)-morpholin-4-yl-methanone (0.7 g) and copper(I) cyanide (2.3 g) in N,N-dimethylformamide were irradiated in a microwave oven at 180° C. for 1.5 hours. To the mixture water (40 ml) and ethyl acetate (40 ml) were added. The solid was filtered and the organic phase was evaporated and dried in vacuum. The product was purified by flash chromatography using heptane-ethyl acetate as an eluent.

$^1$H NMR (DMSO-d$_6$): δ=3.65 (br, 8H), 4.00 (m, 3H), 4.05 (m, 3H), 7.39 (s, 1H).

(3-Chloro-7-cyano-5,6-dihydroxy-benzo[b]thiophen-2-yl)-morpholin-4-yl-methanone (3-Chloro-7-cyano-5,6-dimethoxy-benzo[b]thiophen-2-yl)-morpholin-4-yl-methanone (0.05 g) was suspended in dichloromethane under nitrogen, cooled to −20° C. and treated dropwise with a solution of 1M boron tribromide in dichloromethane. The suspension was stirred at −20° C. for 30 minutes and in cool overnight. The mixture was poured into ice-cold water and stirred at room temperature for 30 minutes. The product was filtered and purified by a preparative plate (reverse phase) using a mixture of toluene, ethyl acetate and acetic acid (8:1:1) as an eluent.

$^1$H NMR (DMSO-d$_6$): δ=3.52 (m, 4H), 3.63 (br, 4H), 7.02 (s, 1H).

As already mentioned hereinbefore, the compounds of formula I show interesting pharmacological properties, namely they exhibit an enhanced catechol-O-methyltransferase (COMT) enzyme inhibiting activity and have an improved bioavailability and/or a prolonged duration of action due to slow elimination via glucuronidation. Furthermore, they do not uncouple oxidative phosphorylation. Said properties are demonstrated with the pharmacological tests presented below.

Experiment 1: Determination of COMT Inhibiting Activity In Vitro

The $K_i$ values were determined by measuring the COMT activity with various drug concentrations using recombinant human soluble form of COMT (hS-COMT). hS-COMT was preincubated with 25 μM S-adenosyl-L-methionine (SAM) and COMT inhibitor in 100 μM Na$_2$HPO$_4$ buffer (pH 7.4) containing 5 μM MgCl$_2$ for 5 min at 37° C. The reaction was started by adding the substrate esculetin (10 μM). The production of O-methylated esculetin was measured as time-resolved fluorescence (excitation at 355 nm, emission at 460 nm) using a FlexStation fluorometer (Molecular Probes, USA). The assay was performed on 96-well plates. The tight binding inhibition constant, $K_i$, was resolved from the reaction kinetics observed at varying inhibitor concentrations using PlateKi software (BioKin, USA).

The results are shown in Table 1. The results show that the compounds of formula I are capable of inhibiting COMT activity in vitro with an efficacy better than or equal to entacapone.

TABLE 1

| COMT inhibiting activity in vitro. | |
| --- | --- |
| Compound | $K_i$/nM |
| Compound of example 4 | 0.5 |
| Compound of example 5 | 1.5 |
| Compound of example 7 | 1.5 |
| Compound of example 8 | 0.6 |
| Compound of example 12 | 0.6 |
| Compound of example 13 | 0.2 |
| Compound of example 16 | 0.9 |
| Compound of example 23 | 2.0 |
| Entacapone | 1.9 |

Experiment 2: Determination of Metabolic Stability In Vitro

The metabolic stability was studied by incubating the compounds together with human liver microsomes (Human Biologics Inc.) using uridine-5'-diphosphoglucuronic acid (UDPGA, Sigma) as a cofactor. The incubation was carried out in 100 mM phosphate buffer (pH 7.4) containing 5 mM $MgCl_2$. The final test substance concentration was 100 µM and the microsomal protein amount was 0.4 mg/ml. After 5 min pre-incubation the reaction was started with pre-warmed UDPGA, final concentration 5 mM. The mixture was incubated in Eppendorf tubes for 60 min at 37° C., and the reaction was terminated either by adding methanol or perchloric acid/methanol (1:9) mixture. After protein precipitation the glucuronide formed was separated by high-performance liquid chromatography (HPLC). The area of the glucuronide in the HPLC chromatogram was compared to that formed from entacapone in the same experimental conditions to obtain a relative glucuronidation value for each compound.

The results are shown in Table 2. The results show that the compounds of formula I possess increased metabolic stability compared to entacapone in respect of glucuronidation. Glucuronidation has been shown to be the major elimination route of entacapone and thus the compounds of formula I have an improved bioavailability and/or a prolonged duration of action.

TABLE 2

Metabolic stability in vitro (relative glucuronidation; entacapone = 1.00).

| Compound | Relative glucuronidation |
| --- | --- |
| Compound of example 4 | <0.01 |
| Compound of example 12 | 0.03 |
| Compound of example 16 | <0.01 |
| Compound of example 23 | 0.26 |
| Entacapone | 1.00 |

Experiment 3: Determination of Uncoupling of Oxidative Phosphorylation In Vitro

Uncoupling of oxidative phosphorylation was studied in isolated rat liver mitochondria measuring the oxygen consumption by a fluorescent technique.

The mitochondrial preparations were made as described in Nissinen et al. *European Journal of Pharmacology*, 340 (1997) 287. Shortly, a rat was decapitated, liver was excised, washed in ice cold 0.9% NaCl and cut into pieces. The tissue was placed into 40 ml of homogenization buffer containing 2 mM Tris-HCl, 0.25 M sucrose, 0.1 mM EDTA pH 6.8 (1:4 w/vol) and homogenized with 5-20 strokes (800 rpm) in a medium-fitting Teflon-in-glass Braun homogenizator. The homogenate was centrifuged at 1000 g for 10 min at 4° C. The supernatant was collected and centrifuged at 8200 g for 10 min at 4° C. The supernatant was discarded and the pellet was washed twice with 10 ml of homogenization buffer. The suspension was centrifuged at 8200 g for 10 min at 4° C. The supernatant was discarded and the pellet was suspended into 2 ml of homogenization buffer and kept in ice until use (up to 2-6 hours). The protein concentration was measured.

BD™ oxygen Biosensor 96 microwell plates were used for measuring oxygen consumption of mitochondria. The microwell plate has an oxygen sensitive fluorescent compound (Tris 1,7-diphenyl-1,10-phenanthroline ruthenium(II) chloride) embedded in the gas permeable bottom of the well. Oxygen inhibits dye's fluorescence so the oxygen consumption of mitochondria is detected as an increase in fluorescence.

The test compounds were added into the assay plate at various final concentrations (1, 2.5, 5, 10, 25, 50 µM). A known uncoupler of mitochondrial oxidative phosphorylation, dinitrophenol (DNP; 10 µM), was used as a reference compound (cf. Hemker *Biochimica et Biophysica Acta*, 81 (1964) 1, Nissinen et al. *European Journal of Pharmacology*, 340 (1997) 287). The control contained only 2% DMSO. A stock solution of mitochondria (0.72 ml=4 mg/protein/ml) was added into 2.28 ml of respiratory buffer (37° C.) containing 250 mM saccharose, 5 mM $Na_2HPO_4$, 2 mM $MgCl_2$, 1 mM EGTA, 5 mM sodium succinate and 10 mM MOPS pH 7.0. The measurement was started with the addition of the mitochondrial suspension (50 µl/well) to the wells. The plate was stirred for 20 s and the fluorescence in the wells was measured for 10 min using 9 s interval, excitation at 485 nm, emission at 630 nm and emission cut off at 610 nm. The photomultiplier tube sensitivity option was set to "low".

The slope factor of each oxygen consumption measurement was determined. The means of two replicates were divided by the means of six control values, and the threshold values of uncoupling were determined for the compounds. The DNP/Control ratios describe the activity of mitochondria.

If a sample/Control slope ratio exceeded 2, it was interpreted as uncoupling of oxidative phosphorylation. As a control for assay quality, DNP/Control ratios were calculated, which gives the activity of mitochondria. Only assays where DNP/Control ratio was larger than 4 were considered acceptable and used in tests.

The results are shown in Table 3. The results show that the compounds of formula I do not uncouple oxidative phosphorylation. The compounds of formula I thus possess a desirable safety profile.

TABLE 3

Uncoupling of oxidative phosphorylation in vitro.

| Compound | Uncoupling/µM |
| --- | --- |
| Compound of example 4 | >50 |
| Compound of example 12 | >50 |
| Compound of example 13 | >50 |
| Compound of example 23 | >50 |
| DNP | 10 |
| Tolcapone | 2.6 |

The compounds of formula I exhibit COMT inhibiting activity. The present invention thus provides compounds, or salts or esters thereof, for use as a medicament. Furthermore, a method for the treatment of diseases or conditions wherein COMT inhibiting agents are indicated to be useful is provided. For example, a method for the treatment of Parkinson's disease, such as potentiation of levodopa therapy or therapy with another dopamine precursor, is provided. In said method a therapeutically effective amount of at least one compound of formula I is administered to a subject in need of such treatment. The use of the compounds of formula I for the manufacture of a medicament for the treatment of diseases or conditions wherein COMT inhibiting agents are indicated to be useful, e.g. Parkinson's disease, is also provided.

The compounds of formula I can be administered, for example, enterally, topically or parenterally by means of any pharmaceutical formulation useful for said administration and containing at least one active compound of formula I in pharmaceutically acceptable and effective amounts together with pharmaceutically acceptable diluents, carriers and/or excipients known in the art.

The therapeutic dose to be given to a patient in need of the treatment will vary depending on the compound being administered, the age and the sex of the subject being treated, the particular condition being treated, as well as the route and method of administration, and is easily determined by a person skilled in the art. Accordingly, the typical dosage for oral administration is from 5 μg/kg to 100 mg/kg per day and for parenteral administration from 0.5 μg/kg to 10 mg/kg for an adult mammal.

The compounds according to this invention are given to a patient as such or in combination with one or more other active ingredients and/or suitable pharmaceutical excipients. The latter group comprises conventionally used excipients and formulation aids, such as fillers, binders, disintegrating agents, lubricants, solvents, gel forming agents, emulsifiers, stabilizers, colorants and/or preservatives.

The compounds of formula I are formulated into dosage forms using commonly known pharmaceutical manufacturing methods. The dosage forms can be e.g. tablets, capsules, granules, suppositories, emulsions, suspensions or solutions. Depending on the route of administration and the galenic form, the amount of the active ingredient in a formulation can typically vary between 0.01% and 100% (w/w).

For the treatment of Parkinson's disease the compounds of formula I can be given together with levodopa or another dopamine precursor, each in its own composition or combined in a single composition. Also a dopa decarboxylase (DDC) inhibitor, such as benserazide or carbidopa, and/or a monoamine oxidase type B (MAO-B) inhibitor, such as lazabemide, rasagiline, safinamide or selegiline, can be present. The amount of levodopa can be from 50 mg to 400 mg, e.g. from 50 mg to 300 mg, such as from 50 mg to 200 mg. The amount of carbidopa can be from 5 mg to 200 mg, e.g. from 5 mg to 100 mg, such as from 5 mg to 50 mg.

The DDC inhibitor and the dopamine precursor, such as levodopa, are typically administered in a ratio of from 1:1 to 1:40, e.g. from 1:4 to 1:10.

The daily dose of lazabemide is typically from 100 mg to 800 mg, e.g. from 100 mg to 200 mg, divided into 1 to 10 individual doses, e.g. 1 to 2 individual doses. The daily dose of rasagiline is typically from 0.1 mg to 5 mg, e.g. from 0.5 mg to 2 mg, divided into 1 to 10 individual doses, e.g. 1 to 2 individual doses. The daily dose of safinamide is typically from 10 mg to 600 mg, e.g. from 50 mg to 150 mg, divided into 1 to 10 individual doses, e.g. 1 to 2 individual doses. The daily dose of selegiline is typically from 1 mg to 20 mg, e.g. from 2 mg to 10 mg, divided into 1 to 10 individual doses, e.g. 1 to 2 individual doses.

A person skilled in the art will appreciate that the embodiments described in this application can be modified without departing from the inventive concept. A person skilled in the art also understands that the invention is not limited to the particular embodiments disclosed but is intended to also cover modifications of the embodiments that are within the spirit and scope of the invention.

The invention claimed is:
1. A compound of formula I:

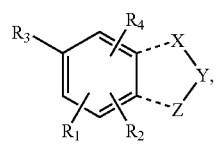

wherein
$R_2$ is in a position ortho to $R_3$, and $R_1$ is in a position ortho to $R_2$; or $R_1$ is in a position ortho to $R_3$, and $R_4$ is in a position ortho to $R_1$;
$R_1$ is cyano or nitro;
$R_2$ is hydroxy;
$R_3$ is hydroxy;
$R_4$ is H, $(C_1$-$C_6)$alkyl, halo$(C_1$-$C_6)$alkyl, cyano, formyl, $(C_1$-$C_6)$alkyl-(C=O)—, halogen, or nitro;
the dotted line is a single or a double bond;
two of X, Y, or Z are $CR_5(R_6)_m$; and one of X, Y, or Z is S or one of X, Y, or Z is $CR_5(R_6)_m$, one of X, Y, or Z is $N(R_7)_n$, and one of X, Y, or Z is S;
m is, independently at each occurrence, 0 or 1;
n is 0, 1, or 2;
$R_5$ is, independently at each occurrence, H, $(C_1$-$C_6)$alkyl, $(C_2$-$C_6)$alkenyl, halogen, hydroxy, $(C_1$-$C_5)$alkoxy, halo$(C_1$-$C_6)$alkyl, hydroxy$(C_1$-$C_6)$alkyl, $(C_1$-$C_6)$alkyl-(C=O)—, $(C_1$-$C_8)$alkoxy-(C=O)—, cyano, formyl, $(C_1$-$C_6)$alkyl-(C=S), $(R_8)_2N$—(C=S)—, $R_8$—(C=NR$_8$)—, carboxy, $(C_3$-$C_7)$cycloalkyl, heterocyclyl, aryl, heteroaryl, heterocyclyl-(C=O)—, aryl$(C_1$-$C_6)$alkyl, $(R_8)_2N$—, $(R_8)_2N$—$(C_1$-$C_6)$alkyl, $(R_8)_2N$—(C=O)—, $(C_{1-6})$alkyl-S—, $R_9$—(S=O)—, $R_9$—(O=S=O)—, $(C_1$-$C_6)$alkoxy$(C_1$-$C_6)$alkyl, $(C_1$-$C_6)$alkoxy-(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, hydroxy$(C_1$-$C_6)$alkoxy$(C_1$-$C_6)$alkyl, $(C_1$-$C_6)$alkyl-S—$(C_1$-$C_6)$alkyl, $(C_1$-$C_6)$alkyl-S—(C=O)—, $(C_3$-$C_7)$cycloalkyl$(C_1$-$C_6)$alkyl, aryloxy, aryloxy$(C_1$-$C_6)$alkyl, aryl$(C_1$-$C_6)$alkoxy, aryl$(C_1$-$C_6)$alkoxy$(C_1$-$C_6)$alkyl, or heterocyclyl-(C=S)—, wherein independently at each occurrence the $(C_3$-$C_7)$cycloalkyl, heterocyclyl, aryl, or heteroaryl as such or as part of another group is unsubstituted or substituted with 1, 2, or 3 substituent(s) each independently chosen from $(C_1$-$C_6)$alkyl, halogen, hydroxy, carboxy, $(C_1$-$C_6)$alkoxy, and $(R_8)_2N$—;
$R_6$ is, independently at each occurrence, H, $(C_1$-$C_6)$alkyl, halogen, hydroxy, hydroxy$(C_1$-$C_6)$alkyl, or $(C_1$-$C_6)$alkoxy;
or $R_5$ and $R_6$ both attached to the same carbon ring atom form, together with the carbon ring atom to which they are attached, a —(C=O)— group;
or $R_5$ and $R_6$ both attached to the same carbon ring atom form, together with the carbon ring atom to which they are attached, C=C$(R_8)_2$;
or $R_5$ and $R_6$ both attached to the same carbon ring atom form, together with the carbon ring atom to which they are attached, a 5-, 6-, or 7-membered saturated or unsaturated carbocyclic ring, wherein said ring is unsubstituted or substituted with 1 or 2 substituent(s) each independently chosen from $(C_1$-$C_6)$alkyl, halogen, hydroxy, $(C_1$-$C_6)$alkoxy, and carboxy;
$R_7$ is, independently at each occurrence, H, $(C_1$-$C_6)$alkyl, $(C_3$-$C_7)$cycloalkyl, $(C_1$-$C_6)$alkoxy, aryl, or O$^-$, wherein independently at each occurrence the $(C_3$-$C_7)$cycloalkyl or aryl is unsubstituted or substituted with 1, 2, or 3 substituent(s) each independently chosen from $(C_1$-$C_6)$alkyl, halogen, hydroxy, $(C_1$-$C_6)$alkoxy, and carboxy;
or $R_5$ and $R_5$, $R_5$ and $R_7$, or $R_7$ and $R_7$ attached to adjacent ring atoms form, together with the ring atoms to which they are attached, a condensed 5-, 6-, or 7-membered saturated or unsaturated carbocyclic ring or a condensed 5-, 6-, or 7-membered saturated or unsaturated heterocyclic ring containing 1 or 2 heteroatom(s) chosen from N, O, and S, wherein said carbo- or heterocyclic ring is unsubstituted or substituted with 1 or 2 substituent(s)

each independently chosen from $(C_1-C_6)$alkyl, halogen, hydroxy, $(C_1-C_6)$alkoxy, carboxy, and oxo;

$R_8$ is, independently at each occurrence, H, $(C_1-C_6)$alkyl, $(C_1-C_6)$alkoxy, aryl, or aryl$(C_1-C_6)$alkyl, wherein independently at each occurrence the aryl as such or as part of another group is unsubstituted or substituted with 1 or 2 substituent(s) each independently chosen from $(C_1-C_6)$alkyl, halogen, hydroxy, carboxy, and $(C_1-C_6)$alkoxy;

$R_9$ is, independently at each occurrence, $(C_1-C_6)$alkyl, $(R_8)_2N$—, hydroxy, or $(C_1-C_6)$alkoxy;

or a pharmaceutically acceptable salt or ester thereof.

2. The compound according to claim 1, wherein $R_2$ is in a position ortho to $R_3$, and $R_1$ is in a position ortho to $R_2$.

3. The compound according to claim 1, wherein $R_1$ is in a position ortho to $R_3$, and $R_4$ is in a position ortho to $R_1$.

4. The compound according to claim 1, wherein $R_4$ is H, halogen, or nitro.

5. The compound according to claim 4, wherein $R_4$ is H.

6. The compound according to claim 1, wherein $R_1$ is cyano.

7. The compound according to claim 1, wherein $R_1$ is nitro.

8. The compound according to claim 1, wherein one of the dotted lines is a double bond.

9. The compound according to claim 1, wherein one of X, Y, or Z is $CR_5(R_6)_m$, one of X, Y, or Z is $N(R_7)_n$, and one of X, Y, or Z is S.

10. The compound according to claim 1, wherein two of X, Y, or Z are $CR_5(R_6)_m$, and one of X, Y, or Z is S.

11. The compound according to claim 1, wherein $R_7$ is, independently at each occurrence, H, $(C_1-C_6)$alkyl, or aryl, wherein independently at each occurrence the aryl is unsubstituted or substituted with 1, 2, or 3 substituent(s) each independently chosen from a halogen.

12. The compound according to claim 1,
wherein
$R_5$ is, independently at each occurrence, H, $(C_1-C_6)$alkyl, halogen, halo$(C_1-C_6)$alkyl, $(C_1-C_8)$alkoxy-(C=O)—, carboxy, aryl, heteroaryl, heterocyclyl-(C=O)— or $(R_8)_2N$—(C=O)—, wherein independently at each occurrence the heterocyclyl, aryl, or heteroaryl as such or as part of another group is unsubstituted or substituted with 1, 2 or 3 substituent(s) each independently chosen from $(C_1-C_6)$alkyl and hydroxy;

$R_6$ is, independently at each occurrence, H;
or $R_5$ and $R_6$ both attached to the same carbon ring atom form, together with the carbon ring atom to which they are attached, a —(C=O)— group;

$R_8$ is, independently at each occurrence, $(C_1-C_6)$alkyl or aryl, wherein independently at each occurrence the aryl is unsubstituted or substituted with 1 or 2 substituent(s) each independently chosen from carboxy and $(C_1-C_6)$alkoxy.

13. The compound according to claim 12, wherein
m is, independently at each occurrence, 0;
$R_5$ is, independently at each occurrence, H, halogen, $(C_1-C_6)$alkoxy-(C=O)—, carboxy, heterocyclyl-(C=O)— or $(R_6)_2N$—(C=O)—, wherein independently at each occurrence the heterocyclyl as part of another group is unsubstituted or substituted with 1, 2, or 3 substituent(s) each independently chosen from $(C_1-C_6)$alkyl, and hydroxy;
$R_8$ is, independently at each occurrence, $(C_1-C_6)$alkyl or aryl, wherein independently at each occurrence the aryl is unsubstituted or substituted with 1 substituent chosen from carboxy and $(C_1-C_6)$alkoxy.

14. The compound according to claim 1, wherein the compound is 7-nitro-2-pyridin-4-yl-benzothiazole-5,6-diol methane sulfonate, 3-chloro-5,6-dihydroxy-7-nitrobenzo[b]thiophene-2-carboxylic acid, 3-chloro-5,6-dihydroxy-7-nitrobenzo[b]thiophene-2-carboxylic acid ethyl ester, 3-chloro-5,6-dihydroxy-4-nitrobenzo[b]thiophene-2-carboxylic acid, 3-chloro-5,6-dihydroxy-7-nitrobenzo[b]thiophene, (3-chloro-5,6-dihydroxy-7-nitro-benzo[b]thiophen-2-yl)-morpholin-4-yl-methanone, 3-chloro-5,6-dihydroxy-7-nitro-benzo[b]thiophene-2-carboxylic acid diethylamide, (3-chloro-5,6-dihydroxy-7-nitrobenzo[b]thiophen-2-yl)-piperidin-1-yl-methanone, 3-chloro-5,6-dihydroxy-7-nitro-benzo[b]thiophene-2-carboxylic acid phenylamide, 3-[(3-chloro-5,6-dihydroxy-7-nitro-benzo[b]thiophene-2-carbonyl)-amino]-benzoic acid, 4-[(3-chloro-5,6-dihydroxy-7-nitro-benzo[b]thiophene-2-carbonyl)-amino]-benzoic acid, 3-chloro-5,6-dihydroxy-7-nitro-benzo[b]thiophene-2-carboxylic acid (4-methoxy-phenyl)amide, 2-methyl-7-nitro-benzothiazole-5,6-diol, (5,6-dihydroxy-7-nitro-benzo[b]thiophen-2-yl)-morpholin-4-yl-methanone, 5,6-dihydroxy-7-nitro-benzo[b]thiophene-2-carboxylic acid, 5,6-dihydroxy-2-methyl-7-nitrobenzo[d]isothiazol-3-one, (5,6-dihydroxy-3-methyl-7-nitro-benzo[b]thiophen-2-yl)morpholin-4-yl-methanone, 5,6-dihydroxy-7-nitro-benzo[b]thiophene-2-carboxylic acid ethyl ester, nitro-2-phenyl-benzothiazole-5,6-diol, 6,7-dihydroxy-5-nitro-benzo[b]thiophene-2-carboxylic acid methyl ester, 1-(5,6-dimethoxy-7-nitro-benzo[b]thiophen-2-yl)-nonan-1-one, (3-chloro-5,6-dihydroxy-4,7-dinitrobenzo[b]thiophen-2-yl)-morpholin-4-yl-methanone, (3,4-chloro-5,6-dihydroxy 7-dinitro-benzo[b]thiophen-2-yl)-morpholin-4-yl-methanone, (3-chloro-5,6-dihydroxy-4-nitro-benzo[b]thiophen-2-yl)-morpholin-4-yl-methanone, (3-chloro-5,6-dihydroxy-7-nitro-benzo[b]thiophen-2-yl)-(2,6-dimethyl-morpholin-4-yl)-methanone, (3-chloro-5,6-dihydroxy-7-nitro-benzo[b]thiophen-2-yl)-(4-hydroxypiperidin-1-yl)-methanone, (3-bromomethyl-5,6-dihydroxy-7-nitrobenzo[b]thiophen-2-yl)-morpholin-4-yl-methanone, 5,6-dihydroxy-3-methyl-2-(morpholine-4-carbonyl)-benzo[b]thiophene-4-carbonitrile, or (3-chloro-5,6-dihydroxy-7-cyano-benzo[b]thiophen-2-yl)-morpholin-4-yl-methanone.

15. A pharmaceutical composition comprising as active ingredient at least one compound according to a compound of formula I:

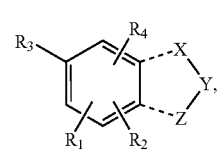

wherein
$R_2$ is in a position ortho to $R_3$ and $R_1$ is in a position ortho to $R_2$, or $R_1$ is in a position ortho to $R_3$ and $R_4$ is in a position ortho to $R_1$;
$R_1$ is cyano or nitro;
$R_2$ is hydroxy;
$R_3$ is hydroxy;
$R_4$ is H, $(C_1-C_8)$alkyl, halo$(C_1-C_5)$alkyl, cyano, formyl, $(C_1-C_6)$alkyl-(C=O)—, halogen, or nitro;
the dotted line is a single or a double bond;
two of X, Y, or Z are $CR_5(R_6)_m$, and one of X, Y, or Z or one of X, Y, or Z is $CR_5(R_6)_m$, one of X, Y, or Z is $N(R_7)_n$, and one of X, Y, or Z is S;

m is, independently at each occurrence, 0 or 1;
n 0, 1, or 2;
$R_5$ is, independently at each occurrence, H, $(C_1-C_6)$alkyl, $(C_2-C_6)$alkenyl, halogen, hydroxy, $(C_1-C_6)$alkoxy, halo$(C_1-C_6)$alkyl, hydroxy$(C_1-C_6)$alkyl, $(C_1-C_6)$alkyl-(C=O)—, $(C_1-C_8)$alkoxy-(C=O)—, cyano, formyl, $(C_1-C_6)$alkyl-(C=S)—, $(R_8)_2$N—(C=S)—, $R_8$—(C=NR$_8$)—, carboxy, $(C_3-C_7)$cycloalkyl, heterocyclyl, aryl, heteroaryl, heterocyclyl-(C=O)—, aryl$(C_1-C_6)$alkyl, $(R_8)_2$N—, $(R_8)_2$N—$(C_1-C_6)$alkyl, $(R_8)_2$N—(C=O)—, $(C_1-C_6)$alkyl-S—, $R_9$—(S=O)—, $R_9$—(O=S=O)—, $(C_1-C_6)$alkoxy$(C_1-C_6)$alkyl, $(C_1-C_6)$alkoxy-(C=O)—$(C_1-C_6)$alkyl, $(C_1-C_6)$alkyl-(C=O)—O—, $(C_1-C_6)$alkyl-(C=O)—O—$(C_1-C_6)$alkyl, hydroxy$(C_1-C_6)$alkoxy$(C_1-C_6)$alkyl, $(C_1-C_6)$alkyl-S—$(C_1-C_6)$alkyl, $(C_1-C_6)$alkyl-S—(C=O)—, $(C_3-C_7)$cycloalkyl$(C_1-C_6)$alkyl, aryloxy, aryloxy$(C_1-C_6)$alkyl, aryl$(C_1-C_6)$alkoxy, aryl$(C_1-C_6)$alkoxy$(C_1-C_6)$alkyl, or heterocyclyl-(C=S)—, wherein independently at each occurrence the $(C_3-C_7)$cycloalkyl, heterocyclyl, aryl, or heteroaryl as such or as part of another group is unsubstituted or substituted with 1, 2, or 3 substituent(s) each independently chosen from $(C_1-C_6)$alkyl, halogen, hydroxy, carboxy, $(C_1-C_6)$alkoxy, and $(R_8)_2$N—;
$R_6$ is, independently at each occurrence, H, $(C_1-C_6)$alkyl, halogen, hydroxy, hydroxy$(C_1-C_6)$alkyl or $(C_1-C_6)$alkoxy;
or $R_5$ and $R_6$ both attached to the same carbon ring atom form, together with the carbon ring atom to which they are attached, a —(C=O)— group;
or $R_5$ and $R_6$ both attached to the same carbon ring atom form, together with the carbon ring atom to which they are attached, C=C(R$_8$)$_2$;
or $R_5$ and $R_6$ both attached to the same carbon ring atom form, together with the carbon ring atom to which they are attached, a 5-, 6-, or 7-membered saturated or unsaturated carbocyclic ring, wherein said ring is unsubstituted or substituted with 1 or 2 substituent(s) each independently chosen from $(C_1-C_6)$alkyl, halogen, hydroxy, $(C_1-C_6)$alkoxy and carboxy;
$R_7$ is, independently at each occurrence, H, $(C_1-C_6)$alkyl, $(C_3-C_7)$cycloalkyl, $(C_1-C_6)$alkoxy, aryl or O$^-$, wherein independently at each occurrence the $(C_3-C_7)$cycloalkyl or aryl is unsubstituted or substituted with 1, 2, or 3 substituent(s) each independently chosen from $(C_1-C_6)$alkyl, halogen, hydroxy, $(C_1-C_6)$alkoxy and carboxy;
or $R_5$ and $R_5$, $R_5$ and $R_7$, or $R_7$ and $R_7$ attached to adjacent ring atoms form, together with the ring atoms to which they are attached, a condensed 5-, 6-, or 7-membered saturated or unsaturated carbocyclic ring or a condensed 5-, 6-, or 7-membered saturated or unsaturated heterocyclic ring containing 1 or 2 heteroatom(s) chosen from N, O, and S, wherein said carbo- or heterocyclic ring is unsubstituted or substituted with 1 or 2 substituent(s) each independently chosen from $(C_1-C_6)$alkyl, halogen, hydroxy, $(C_1-C_6)$alkoxy, carboxy and oxo;
$R_8$ is, independently at each occurrence, H, $(C_1-C_6)$alkyl, $(C_1-C_6)$alkoxy, aryl or aryl$(C_1-C_6)$alkyl, wherein independently at each occurrence the aryl as such or as part of another group is unsubstituted or substituted with 1 or 2 substituent(s) each independently chosen from $(C_1-C_6)$alkyl, halogen, hydroxy, carboxy and $(C_1-C_6)$alkoxy;
$R_9$ is, independently at each occurrence, $(C_1-C_6)$alkyl, $(R_8)_2$N—, hydroxy, or $(C_1-C_6)$alkoxy;
or a pharmaceutically acceptable salt or ester thereof;
and a pharmaceutically acceptable carrier, diluent, excipient, or a mixture thereof.

16. The pharmaceutical composition according to claim 15, wherein the composition comprises further at least one other active ingredient.

17. The pharmaceutical composition according to claim 15, wherein the composition further comprises levodopa and carbidopa.

18. A method for the treatment of Parkinson's disease comprising administering to a mammal in need of such treatment an effective amount of at least one compound according to a compound of formula I:

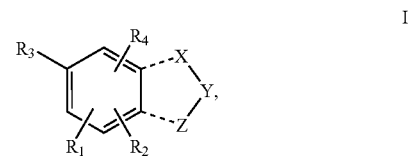

I wherein
$R_2$ is in a position ortho to $R_3$, and $R_1$ is in a position ortho to $R_2$; or $R_1$ is in a position ortho to $R_3$, and $R_4$ is in a position ortho to $R_1$;
$R_1$ is cyano or nitro;
$R_2$ is hydroxy;
$R_3$ is hydroxy;
$R_4$ is H, $(C_1-C_6)$alkyl, halo$(C_1-C_6)$alkyl, cyano, formyl, $(C_1-C_6)$alkyl-(C=O)—, halogen, or nitro;
the dotted line is a single or a double bond;
two of X, Y, or Z are CR$_5$(R$_6$)$_m$; and one of X, Y, or Z is S or one of X, Y, or Z is CR$_5$(R$_6$)$_m$, one of X, Y, or Z is N(R$_7$)$_n$, and one of X, Y, or Z is S;
m is, independently at each occurrence, 0 or 1;
n is 0, 1, or 2;
$R_5$ is, independently at each occurrence, H, $(C_1-C_6)$alkyl, $(C_2-C_6)$alkenyl, halogen, hydroxy, $(C_1-C_6)$alkoxy, halo$(C_1-C_6)$alkyl, hydroxy$(C_1-C_6)$alkyl, $(C_1-C_6)$alkyl-(C=O)—, $(C_1-C_8)$alkoxy-(C=O)—, cyano, formyl, $(C_1-C_6)$alkyl-(C=S)—, $(R_8)_2$N—(C=S)—, $R_8$—(C=NR$_8$)—, carboxy, $(C_3-C_7)$cycloalkyl, heterocyclyl, aryl, heteroaryl, heterocyclyl-(C=O)—, aryl$(C_1-C_6)$alkyl, $(R_8)_2$N—, $(R_3)_2$N—$(C_1-C_6)$alkyl, $(R_8)_2$N—(C=O)—, $(C_1-C_6)$alkyl-S—, $R_9$—(S=O)—, $R_9$—(O=S=O)—, $(C_1-C_6)$alkoxy$(C_1-C_6)$alkyl, $(C_1-C_6)$alkoxy-(C=O)—$(C_1-C_6)$alkyl, $(C_1-C_6)$alkyl-(C=O)—O—, $(C_1-C_6)$alkyl-(C=O)—O—$(C_1-C_6)$alkyl, hydroxy$(C_1-C_6)$alkoxy$(C_1-C_6)$alkyl, $(C_1-C_6)$alkyl-S—$(C_1-C_6)$alkyl, $(C_1-C_6)$alkyl-S—(C=O)—, $(C_3-C_7)$cycloalkyl$(C_1-C_6)$alkyl, aryloxy, aryloxy$(C_1-C_6)$alkyl, aryl$(C_1-C_6)$alkoxy, aryl$(C_1-C_6)$alkoxy$(C_1-C_6)$alkyl, or heterocyclyl-(C=S)—, wherein independently at each occurrence the $(C_3-C_7)$cycloalkyl, heterocyclyl, aryl, or heteroaryl group is unsubstituted or substituted with 1, 2, or 3 substituent(s) each independently chosen from $(C_1-C_6)$alkyl, halogen, hydroxy, carboxy, $(C_1-C_6)$alkoxy, and $(R_8)_2$N—;
$R_6$ is, independently at each occurrence, H, $(C_1-C_6)$alkyl, halogen, hydroxy, hydroxy$(C_1-C_6)$alkyl, or $(C_1-C_6)$alkoxy;
or $R_5$ and $R_6$ both attached to the same carbon ring atom form, together with the carbon ring atom to which they are attached, a —(C=O)— group;
or $R_5$ and $R_6$ both attached to the same carbon ring atom form, together with the carbon ring atom to which they are attached, C=C(R$_8$)$_2$;

or $R_5$ and $R_6$ both attached to the same carbon ring atom form, together with the carbon ring atom to which they are attached, a 5-, 6-, or 7-membered saturated or unsaturated carbocyclic ring, wherein said ring is unsubstituted or substituted with 1 or 2 substituent(s) each independently chosen from $(C_1-C_6)$alkyl, halogen, hydroxy, $(C_1-C_6)$alkoxy and carboxy;

$R_7$ is, independently at each occurrence, H, $(C_1-C_6)$alkyl, $(C_3-C_7)$cycloalkyl, $(C_1-C_6)$alkoxy, aryl, or $O^-$, wherein independently at each occurrence the $(C_3-C_7)$cycloalkyl or aryl is unsubstituted or substituted with 1, 2, or 3 substituent(s) each independently chosen from $(C_1-C_6)$alkyl, halogen, hydroxy, $(C_1-C_6)$alkoxy and carboxy;

or $R_5$ and $R_5$, $R_5$ and $R_7$, or $R_7$ and $R_7$ attached to adjacent ring atoms form, together with the ring atoms to which they are attached, a condensed 5-, 6-, or 7-membered saturated or unsaturated carbocyclic ring or a condensed 5-, 6-, or 7-membered saturated or unsaturated heterocyclic ring containing 1 or 2 heteroatom(s) chosen from N, O, and S, wherein said carbo- or heterocyclic ring is unsubstituted or substituted with 1 or 2 substituent(s) each independently chosen from $(C_1-C_6)$alkyl, halogen, hydroxy, $(C_1-C_6)$alkoxy, carboxy, and oxo;

$R_8$ is, independently at each occurrence, H, $(C_1-C_6)$alkyl, $(C_1-C_6)$alkoxy, aryl, or aryl$(C_1-C_6)$alkyl, wherein independently each occurrence the aryl group is unsubstituted or substituted with 1 or 2 substituent(s) each independently chosen from $(C_1-C_6)$alkyl, halogen, hydroxy, carboxy, and $(C_1-C_6)$alkoxy;

$R_9$ is, independently at each occurrence, $(C_1-C_6)$alkyl, $(R_6)_2N-$, hydroxy, or $(C_1-C_6)$alkoxy;

or a pharmaceutically acceptable salt or ester thereof.

19. The method according to claim 18, wherein levodopa therapy is potentiated.

20. The compound according to claim 1, wherein the compound is (3-chloro-5,6-dihydroxy-7-nitro-benzo[b]thiophen-2-yl)-morpholin-4-yl-methanone.

21. The compound according to claim 1, wherein the compound is 3-chloro-5,6-dihydroxy-7-nitro-benzo[b]thiophene-2-carboxylic acid diethylamide.

22. The compound according to claim 1, wherein the compound is (3-chloro-5,6-dihydroxy-7-nitro-benzo[b]thiophen-2-yl)-piperidin-1-yl-methanone.

23. The compound according to claim 1, wherein the compound is 3-chloro-5,6-dihydroxy-7-nitro-benzo[b]thiophene-2-carboxylic acid phenylamide.

24. The compound according to claim 1, wherein the compound is 3-[(3-chloro-5,6-dihydroxy-7-nitro-benzo[b]thiophene-2-carbonyl)-amino]-benzoic acid.

25. The compound according to claim 1, wherein the compound is 4-[(3-chloro-5,6-dihydroxy-7-nitro-benzo[b]thiophene-2-carbonyl)-amino]-benzoic acid.

26. The compound according to claim 1, wherein the compound is 3-chloro-5,6-dihydroxy-7-nitro-benzo[b]thiophene-2-carboxylic acid (4-methoxy-phenyl)amide.

27. The compound according to claim 1, wherein the compound is (3-chloro-5,6-dihydroxy-7-nitro-benzo[b]thiophen-2-yl)-(2,6-dimethyl-morpholin-4-yl)-methanone.

28. The compound according to claim 1, wherein the compound is (3-chloro-5,6-dihydroxy-7-nitro-benzo[b]thiophen-2-yl)-(4-hydroxy-piperidin-1-yl)-methanone.

* * * * *

UNITED STATES PATENT AND TRADEMARK OFFICE
CERTIFICATE OF CORRECTION

PATENT NO.         : 8,318,785 B2                                Page 1 of 1
APPLICATION NO.    : 11/995878
DATED              : November 27, 2012
INVENTOR(S)        : Ahlmark et al.

It is certified that error appears in the above-identified patent and that said Letters Patent is hereby corrected as shown below:

Claim 1, col. 40, line 17, "$(C_1-C_5)$alkoxy" should read --$(C_1-C_6)$alkoxy--.

Claim 13, col. 41, lines 57-58, "$(C_1-C_6)$ alkoxy" should read --$(C_1-C_8)$alkoxy--.

Claim 13, col. 41, line 59, "$(R_6)_2N$" should read --$(R_8)_2N$--.

Claim 15, col. 42, line 62, "$(C_1-C_8)$ alkyl" should read --$(C_1-C_6)$ alkyl--.

Claim 15, col. 42, line 62, "$(C_1-C_5)$alkyl" should read --$(C_1-C_6)$alkyl--.

Claim 15, col. 42, line 65, after the second instance of "X,Y, or Z" insert --is S--.

Claim 15, col. 43, line 2, "n 0,1, or 2;" should read --n is 0,1, or 2;--.

Claim 18, col. 44, line 44, "$(R_3)_2N$" should read --$(R_8)_2N$--.

Claim 18, col. 45, line 33, "$(R_6)_2 N$" should read --$(R_8)_2 N$--.

Signed and Sealed this
Twelfth Day of March, 2013

Teresa Stanek Rea
*Acting Director of the United States Patent and Trademark Office*